United States Patent
Metelski

[19]

[11] Patent Number: 6,129,319
[45] Date of Patent: Oct. 10, 2000

[54] AUTOMATICALLY ADJUSTABLE COUNTERBALANCED STAND

[75] Inventor: Andreas Metelski, Romanshorn, Switzerland

[73] Assignee: Leica Microsystems AG, Heerbrugg, Switzerland

[21] Appl. No.: 09/043,404

[22] PCT Filed: Oct. 12, 1996

[86] PCT No.: PCT/EP96/04454

§ 371 Date: May 11, 1998

§ 102(e) Date: May 11, 1998

[87] PCT Pub. No.: WO97/13997

PCT Pub. Date: Apr. 17, 1997

[30] Foreign Application Priority Data

Oct. 12, 1995 [CH] Switzerland ............................ 2976/95

[51] Int. Cl.[7] .................................................. F16M 13/00
[52] U.S. Cl. ........................ 248/123.2; 248/550; 359/384
[58] Field of Search ............................ 248/123.2, 280.1, 248/325, 648, 665, 292.1, 281.1, 550; 359/384

[56] References Cited

U.S. PATENT DOCUMENTS 3,891,301  6/1975  Heller .
5,205,522  4/1993  Nakamura ............................ 248/123.1
5,480,114  1/1996  Nakamura ............................ 248/123.2
5,651,718  7/1997  Nakamura ............................ 248/123.2
5,667,186  9/1997  Luber et al. ............................ 248/550
5,713,545  2/1998  Nakamura ............................ 248/123.1

FOREIGN PATENT DOCUMENTS 0 476 551 A 1  3/1992   European Pat. Off. ........ G02B 21/24
0 628 290 A 1  12/1994  European Pat. Off. ........ A61B 19/02
0 656 194 A 1  6/1995   European Pat. Off. ........ A61B 19/00
  84 00 384 U  2/1984   Germany ........................ A61B 19/00
43 20 443 A 1  12/1994  Germany .

*Primary Examiner*—Ramon O. Ramirez
*Attorney, Agent, or Firm*—Simpson, Simpson & Snyder, LLP

[57] ABSTRACT

Figure 2:
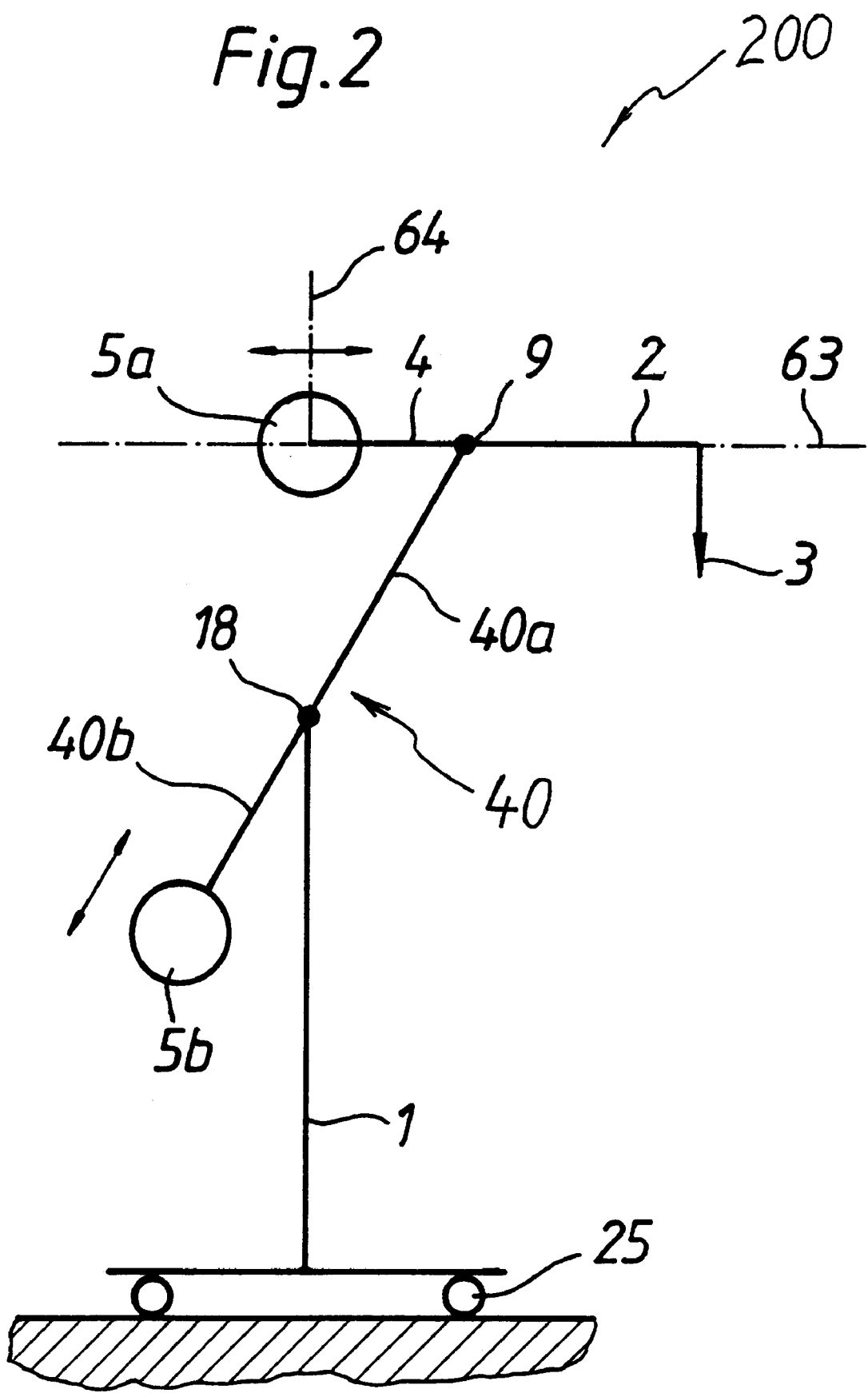

The invention concerns a new kind of stand equipped with two separate balancing weights (5a,b), one of which balances the horizontal pivoting movement and the other of which balances the vertical pivoting movement. Various embodiments relate to electronic measuring means (6) and adjusting means (7) for automatic adjustment of the positions of the balancing weights (5a,b). (FIG. 2)

29 Claims, 17 Drawing Sheets

FIG. 13
FIG. 14
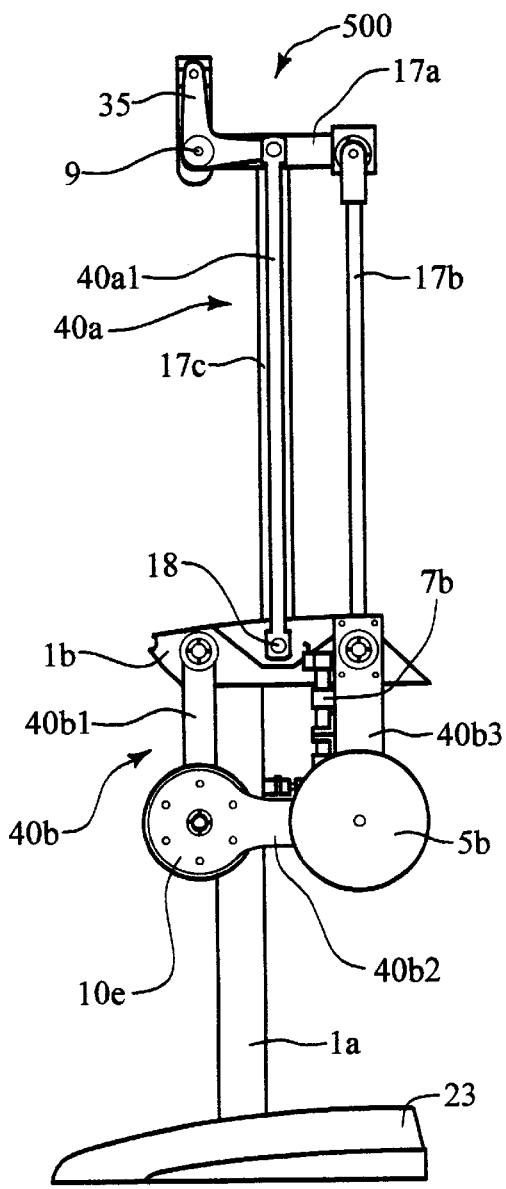
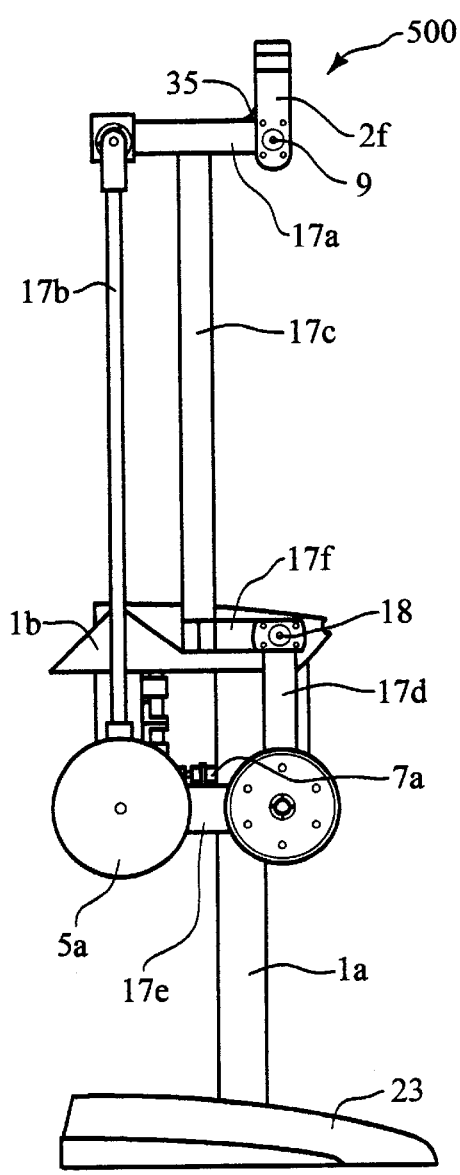

AUTOMATICALLY ADJUSTABLE COUNTERBALANCED STAND

Many designs are known among the stands with adjustable weight compensation having two apparently separated partial weights that are independently adjustable. For example, European Patent Application A-628290 shows such a design. Both weights, though, are necessarily coupled so they can be pivoted only around a common rotating bearing, either around the main rotating bearing or around the main pivot axes which, according to information in the invention, are intended to serve only as bearings for vertical pivoting (as vertical pivot axes) of the stand. Movement of one weight automatically causes movement of the other weight. That was both desirable and intentional at the state of the art, as the attempt was to attain automatic weight compensation over the entire working range of the stand, as long as a weight change on the side of the load was taken into consideration with the compensating weight.

The weight balancing attempted there is based on the theory that optimal weight balancing can only be attained if the point at which the load is applied, the main pivot point, and the center(s) of gravity of (all) the balancing weight(s) all lie on a straight line. This theory is better explained, or more apparent, in the more recent European Patent Application A-656194. In that patent, an attempt is made, with enormous cost in drive technology, to move a single balancing weight directly along that line, in contrast to the disclosure of the former solution. This, however, follows indirectly from the former solution, in that because of the mechanical connection of the partial weights it is always their common center of gravity which was moved along the imaginary line for the compensation or balancing. This theoretical consideration, though, applies in practice only for a certain load weight. Different loads shift the point of load application to the side of this line, causing unbalance.

The Contraves company also marketed a microscope stand with two separate balancing weights. One of them is movable horizontally on a horizontal parallel linking bar which transfers the balancing force. The other is movable vertically on the same kind of structure. Such a stand is also described, for instance, in European Patent Application B-476551. Thus the technology apparently evolved (as this technology is old) in the direction of simplification from two balance weights to just one, but with distinctly more mechanical cost, as mentioned above.

A stand corresponding to the more recent European Patent Application was marketed by the applicant (Mitaka) along with this applicant. With this stand, though, it was found that, contrary to the theory, once the balance was produced it could be maintained only in a limited range of stand position. If the stand, or the load mounted on it, was turned to a different position, imbalance could be noted immediately. This either caused fatigue for the operator, or caused excessive time to be devoted to adjustment while the operator worked with the stand. The change was small only for a very specific load weight.

The objective of this invention is to eliminate that disadvantage. The intent is to find a balancing system that really works optimally. It should maintain balance over a wide working range, so that adjustment is not required during work, or is needed only if the weight of the load itself is changed. An alternative is also suggested for that purpose, with changing geometric dimensions of the stand arm.

To meet the first objective, we go contrary to the current tendency and provide not one, but two separate balancing weights which are, however, newly completely separated from each other functionally. One balancing weight provides the weight balance in the vertical pivoting movement, while the other balancing weight provides the weight balance for the horizontal pivoting movement.

In the sense of the following description, "vertical pivoting movement" always means the pivoting movement of a (vertical) component about the vertical pivot axis (which is itself horizontal) of the stand or pedestal. The stand or pedestal extends to both sides of a vertical plane which contains the vertical pivot axis. "Horizontal pivoting movement" in the sense of the following description, is always a pivoting movement about a pivot axis that is parallel to the vertical pivot axis (horizontal pivot axis). It may be carried by the vertical component, in which case the pivoting movement extends to both sides of an essentially horizontal plane which is perpendicular to the above-mentioned vertical plane, in which the axis is found.

Based on the concept of separating the stand into vertical and horizontal pivot functions, each with independent balancing, there are various special further developments and embodiments within this application which could themselves be applied independently to stands and which could in some circumstances themselves be independent inventions. One preferred embodiment envisages a stand with fully automatic adjustment of the balance, although the invention is not limited to that. The invention also includes purely mechanical stands. The application of the new stand is not limited. In particular, it includes the optical range of close-up and distant magnifications.

These embodiments or further development also solve some problems which are partially independent. That is considered in more detail in the following:

The previously mentioned European Patent Application A-656194 implies that equipping the stand with an automatic measuring and adjusting mechanism has been considered (see Column 2, line 57, to Column 3, line 5).

The practical embodiment, as presented in that European Patent Application (see FIGS. 9 to 13) is apparently not feasible, because this automatic measurement/adjustment mechanism could not be installed in the existing products by the applicant of that European Patent Application.

The recommended solution has unsolved problems from the very beginning. Aside from that, it is not disclosed so that one skilled in the technology could accomplish it without additional information.

The idea that was apparently involved in the cited state of the technology was that of detecting the unbalance and shifting the (single) balancing weight in accordance with the imbalance so as to produce a balance. In contrast, the mechanism suggested there had a kind of pointer. The swing (mutual approach of two parts which can be connected by a coupling) in one direction or another (balance toward or opposite the load) is indicated as with a balance. A photo-optical element detects whether the final position of the pointer is to the left, center, or right. The center position corresponds theoretically to balance, while the left and right positions correspond to imbalance. A positioning drive for the balancing weight is supposed to be controlled on the basis of this information.

Unfortunately, no specific, quantitative information about the imbalance can be gained from this yes/no information.

Quantitative information, on the other hand, would, to the knowledge of the applicant, allow specific adjustments. That is the objective of another aspect of the invention. The invention, accordingly, provides newly that forces or moments which arise from the imbalance are measured so as to be able to make a specific adjustment of the balance weight or weights.

This measure avoids oscillation in the adjustment process, which could in some cases occur with the suggested system. According to the invention, the balance weight is shifted to that position in which the measured value of the forces or moments resulting from the imbalance is approximately zero. This need not necessarily be absolutely zero; it can be a relative value. For instance, given a measurement of bending in a load-bearing arm, a certain bending moment can be detected in the unloaded state. It increases as the load is increased. The adjustment of the balancing weight is controlled, or triggered, according to the invention, by the magnitude of the difference in the bending moment between the unloaded and loaded states. According to one embodiment of the invention, a large difference in the measurements allows rapid adjustment of the balancing weight or weights. Minor imbalances, on the other hand, produce a low-velocity adjustment of the balancing weight.

The specific control of the balancing weight can, for example, be accomplished by a photooptical bar-coded distance meter on the balancing arm, or by monitoring the turning of the drive spindle for the balancing weight. Accurate knowledge of the position of the balancing weight can be accomplished in this variant by automatic zero adjustment of the system (the balancing weight moves automatically to a defined position after the system is turned on), or during operation, in which case the current position of the balancing weight is determined in relation to a base point on the balance arm. In the preferred embodiment of the invention with two independent weights for balancing the vertical and horizontal pivoting movements, the invention is based on new knowledge, according to which a certain balance adjustment for the vertical pivoting movement is necessary before balancing for the horizontal pivoting movement. There are mathematical relations for this. Depending on the type of mutual arrangement of the two balancing weights, they can be expressed in a formula or in a table.

That yields the further aspect of the invention, according to which the automatic adjustment of one balancing weight leads to a likewise automatic adjustment of the second balancing weight. There are, of course, variants within the framework of the invention in which separate measurements can be carried out for the horizontal and vertical balancing movements, which make independent adjustments possible. Such a variant is not preferred, though, to the extent that in working with the stand with a vertical pivoting movement there is an adjustment of the balancing weight which could have been accomplished before the vertical pivoting movement was carried out. Within the framework of the invention, to be sure, there are also mixed forms by which the control of the balancing weight for vertical pivoting movements is based on a formula or table, followed by fine adjustment based on a separate measurement and adjustment through the vertical balancing movement.

Measuring devices designed as torque-measuring devices, which can be placed in the vicinity of arbitrary axes of the stand, provided according to the invention, are particularly advantageous to the extent that two parts which attempt to move toward each other, depending on the imbalance from a pivoting movement, are supported on these axes. That is because the forces produced by the pivoting movement (the unbalanced weight) can be measured at these points as torques, for example. According to the invention, this measurement actuates a brake which blocks the pivoting movement of the parts toward each other. The forces which the brakes absorb must correspond to the torque moments sought. In the unbalanced state, the torsional forces at the brakes are zero. In other words, there is according to the invention a comparative measurement of the torques which result from the bending moments of the load and of the balancing weights.

In one variant of the invention, the forces at the brakes are transferred outward by a measurement arm which is rigidly connected, or which can be braked so as to be rigid, to one of the two parts which can be mutually pivoted toward each other. The forces are held by a rigid support for the other of the two parts. The bending of the measurement arm in this case, which is proportional to the torsion, is measured directly or indirectly on the measurement arm. Strain gauges are used preferably for this. According to a further development of the invention, the measuring arm can have some play with respect to the connection, so that slight pivoting movements can still occur without measurements, while, on the other hand, depending, if desired, on the magnitude of the measurement, different balancing process for the balancing weight(s) can be triggered.

Combinations can be considered as further embodiments, in which, after a certain swing of a measuring arm, a microswitch or the like can be actuated as an emergency switch so that with excessive imbalance (e.g., an operator stumbles and temporarily supports his body weight on the microscope) the balancing weight is immediately shifted to a new position. If necessary, such a microswitch can also be spring-loaded and/or pre-stressed.

It is also possible to measure directly flexing which can occur because of the load on the load arm, by applying strain gauges directly to the load arm or to the balancing arm. One might also consider balance measurements with a photo-optical reading of the bubble of a spirit level for measurements in the unbraked state. A light beam is attenuated by a dark liquid in a spirit level. Only at the position of the air bubble or the like can light pass through well. A planar light sensor is placed behind the level so as to detect the position of the air bubble and transmit it to appropriate control elements.

Combined measuring methods also fall within the limits of the invention. In these methods, for instance, the vertical weight vector of the stand or part of it is measured at a point on the base of the stand, while, at the same time, for example, the angular position of the load arm is measured with respect to the vertical. From those measurements one can calculate the weight of the load, or the change in it, which is a component affecting the weight vector at the point of measurement.

Variants in which only the absolute weight change of the complete stand is measured, so as to determine the change in load weight and to shift the balancing weight(s) depending on that change, are also encompassed by the invention. In such variants, for example, the relative position of the balancing weight with respect to its assigned pivot point is determined as a second measured parameter so that if there is a change in the absolute weight of the stand, which, in the case of the example, would be due only to a change in the weight of the load, the relative position of the appropriate balancing weight is accurately changed.

According to a particular further development of the invention, the measurement and/or shift of the balancing weight is subjected to a time delay. The advantage of that is that the balance can be accomplished relatively free of errors. In the other case, one must assume that during the change in weight of the load (e.g., changing an objective) an operator lays a hand on the load (microscope), and that it remains there briefly after the load change, or an operator, after he has initiated the electrical braking of the stand and tightened it again, still holds the microscope with his hands, so that the weight of the hands could falsify the measurement.

As alternatives to the variants mentioned above, though, there are also possible embodiments in which the balancing weight is permanently adjusted, in which it is found that the precision of the shifting process is of secondary importance and that any externally caused jerky movements of the stand that might occur are compensated immediately. That is, even transient load changes can be compensated continuously through moments of inertia, laying a hand on, or the like.

It is obvious that there can be variants with different rates of movement for the balancing weight within the limits of the invention. (For instance, each movement could proceed by a kind of ramp, with the speed initially high and decreasing continuously or by steps.) It is desirable for them to be controllable from the analog measurements by the measurement system. That is a particular advantage over the known state of the technology according to the cited European Patent Application A-656194, with which practically no yes/no decisions could be made.

Another inventive aspect of the application consists of the selection of a new desirable material for the stand. The disadvantage of the usual stands is that they have a relatively voluminous design, leading to a relatively high total weight for acceptable strength of the stand, and, therefore, to a corresponding load on the floor or ceiling (depending on where they are supported). Another disadvantage of the known stands is the space required for the load arm and the balancing arm, as their geometric dimensions limit the user's working space. According to the invention, parts of the stand are made of sintered or cemented (preferably not epoxy-bonded) fibrous composites such as carbon or carbon fiber composites, aramide fibers, or Kevlar (registered trademark of the du Pont company). That is particularly applicable for the load and/or balancing arm. It was recognized as a special advantage that the composite materials used can, depending on the structures, which can be selected as desired (fiber lay) also have positive influences on the vibrational behavior of the parts, so that the stand can be positioned more directly.

A further inventive aspect is that the cabling which was previously a nuisance on stands, especially for surgical microscopes, can be removed. It has previously been known, partially, that hollow arms could be used as cable ducts. But that has the disadvantage that the cables must be built into the stand, and removed from the hollow arms for service. That is expensive. Due to the measures of the invention, the number of interfaces or plug connections can be reduced, so that the transfer capability of the cable is optimal, even though it is as well protected from outside attack as it would be if it were run through tubing.

According to the invention, the load-carrying members of the stand are built in two parallel parts, so that there is a space between them in which the cable can be placed. The space can be covered by removable cover plates.

One special development of the covers for the cable channel provides a snap fastening for the covers. The snap fasteners can be made in one piece with the covers, by injection molding, for instance, and can fit between the round, preferably tubular, arms with springy snap catches. Screw fastenings or adhesive connections are also possible instead of snap fasteners.

Another aspect of the invention is a different protective or cable channel for the cable leading to the load, usually a microscope. It can itself be used independently, or in combination with the above-mentioned cable channel. According to the invention it is a flexible tube, e.g., a corrugated tube which has a rotatable coupling at its entrance and preferably also at its exit, so that when the load arm is rotated about a vertical axis the corrugated tube can to some extent follow the rotation and so that the tube is not torsionally stressed. The particular advantage of this new cable guide is protecting the cable from mechanical stresses and damage to the cable from external effects. Also, use of the tube reduces the danger of undesired contamination of the cable with germs or the like.

On the other hand, it is simpler to disinfect the tube than the previous cable. It can be made, with no problem, of a material which can be disinfected on its surface by liberal application of a liquid disinfectant. That could be a problem in some circumstances for certain insulating materials for the cables used.

According to a further development of this invention, the length of the tube is divided into two pieces, so that one slotted tube can be placed over another slotted tube. Like the solution with the cable channel, this provides the advantage that the cable channel or tube can be opened if it becomes necessary to perform maintenance on the cables.

According to a further development of this invention, the tube in the vicinity of the load is connected with the stand, or with the load, usually a microscope so that one end of the tube is fastened or connected to the load arm approximately perpendicular its length. This is preferably done so that the tube projects upward and is curved in an arc down to the load, while the other end of the tube is connected with the load or with the microscope in about the direction of the load vector, determined by gravity.

This new mounting gives the following advantages: the cable within the tube is exposed to practically no mechanical load at either end of the tube as the load arm or load moves. Also, the arc of the tube extends, according to the preferred mounting variation, in an area above the stand which causes minimal nuisance to the operator.

No detailed description of the tube used according to the invention is required, as a usable product is itself known and on the market. As an example, see the NW Duplex or Duplex-SVPA corrugated tube offered by Rohrfabrik R üschlikon AG.

Another inventive aspect is that, especially for use of the tube described just above, suction is provided to draw air from the vicinity of the load or the microscope through the tube and other lines connected with it. This has these advantages: danger of possible contamination in the vicinity of the microscope can be reduced in this way because air which might become contaminated is removed and cannot get to the surgical field. With this situation, any elements present which require cooling, such as lamps, electronics, and the like, can be cooled in the flow of removed air.

If a drape is used over the microscope, it can be evacuated according to a new inventive process using the new suction system, or even a different suction system, so that the drape fits optimally to the outside shape of the microscope and stand, and so is the least disturbing to the operators. Furthermore, suction from the region under the drape also prevents outflow of germs or the like, which might have adhered to the microscope or stand, through the closure of the drape.

Another aspect of the invention concerns the problem presented by the usual stands, which are made completely of metal and which are essentially foreign bodies in the operating room. Some attempts have, indeed, been made to shape the arms or parts of the stand so that they leave as much room as possible for the surgical personnel and the treating physicians. That still has not prevented persons bumping into the stand if they move carelessly or if the stand is moved. That could have unpleasant consequences.

The invention is further based on the objective of shaping the stand so as to prevent injuries or damage in case persons bump into it or it strikes walls or other hospital equipment.

This objective is attained through cushioning of the parts, especially the exposed parts that stick out. The preferred embodiment is with use of an integrated form for the cushioning, which has its closed skin toward the room. Integral foam is quite suitable for primary use in the operating room because its surface can be cleaned well and sterilized by liquid or gas.

According to a further development, protective caps are produced from the integral foam, especially to allow service in the areas where there are joints or bends. In connection with the cable channels or tube guides described above, and also independently of them, such protective elements or caps are good protection for cables or the like. The advantages of covering cables, listed above, also apply here.

Obviously, such caps according to the invention can also be used in connection with stands that do not have the features described above or which have any cables guided through tubular arm parts or the like.

A polyurethane foam, for example, can be used as the material of the integral foam.

Another aspect of the invention is directed primarily to the guidance or mounting of a surgical microscope in particular in the vicinity of the point where the load is attached. With the previously mentioned stand from the Mitaka company and in all the ordinary stands, one attempts in principle to attain the position of the center of gravity by having the actual microscope mounted on a slide so that it can be moved left and right to reach the center of gravity, and not just left and right, but also forward and back. Here there are adjusting slides in all three planes. Their adjustment by the operating personnel is somewhat complex and time-consuming.

According to another inventive concept, these adjustments are also automated, by measuring any bending, torsional moments, or her measured parameters at the microscope and making the appropriate shifts of balancing weights. Under some circumstances, with movements in the direction perpendicular to the plane containing the load arm, balance can be measured with a spirit level with optical sensor. In that case the bubble position is measured with optical sensors and the appropriate adjustment is undertaken on that basis.

In the region just mentioned, conventional slides and/or conventional arms or parallelogram guides can be provided or preferably a new kind of chain drive which makes it possible to omit parallelogram controls and still assures that the load is handled with minimal space requirement and hindrance to the operating personnel. Such a new chain drive is described in Swiss Patent Application "mZ. P-3623CH Chain Drive". For the purpose of later combining the teachings of the two applications, the text of the application "R-P-3623-CH is expressly considered also to be disclosed herein, as the text of this application is considered disclosed in the later one.

A further aspect of the invention refers to the problem of transporting stands with relatively large and extended arms. It is known that stands are supported on pedestals and feet on wheels. They are usually fixed with respect to the floor by blocking the wheels or by lowering feet or the like. This is referred to, for instance, in German Utility Patent 8400384.7. When the stand is moved it usually rolls on its wheels. On passing through doors or the like, the size of the stand can be an obstacle. Of course, the load or balancing arm could be swung into a position that reduces the space required for the stand, but something better is desirable.

This problem is solved in this invention by the design possibility of lowering the pedestal of the stand or the arm on the stand with respect to the pedestal and/or the ability to lower at least one of the wheels supporting the foot, so that the stand has slanted position during transport, which further reduces its transportation height and lowers the center of gravity.

In connection with the ability to rotate the stand about a vertical axis, which is required for working with the stand, the invention has dealt with another basically independent problem and has solved it satisfactorily: the size of the stand is also determined by the sizes of its parts and by the number of individual parts needed. Ability to rotate the stand about the vertical axis mentioned has previously required two bearings, each in a horizontal plane. That incurred the need for a tubular housing which held the bearings and, in them, the pedestal. As the shell itself contributed nothing to strength in the vertical direction, but was responsible for transfer of the tilt moment when the stand was unbalanced, it had to be designed to be appropriately massive, so that it was also heavy. Reduction of the shell diameter and the replacement of ball bearings by a normal friction bearing did, to be sure, result in a minor reduction in the stand diameter, but it increased the friction, thus reducing operator comfort.

By contrast, a new inventive solution provides for supporting the pedestal on the foot by means of a crossed roller bearing. It is optimal, especially with respect to the small number of rotations of the stand about its vertical axis, and can be wear-free. The crossed roller bearing can be integrated well in the foot of the stand because of its low structural height, so that the stand can be rotated about its vertical axis quite easily and without hindrance. The volume of the pedestal is further reduced in comparison with the known ones.

Another aspect of the invention concerns the automatic braking used in the joints of the stand to fix the arms, or parts of the arms, in their relative positions. One known brake is presented, for example, in FIGS. 12 and 13 of the previously mentioned European Patent Application A-656 194. Compression springs force the brake disk against a counterpart in such a way that two brake disks are clamped between them. An electromagnet is mounted at one side. In its excited state it pulls on the brake disk, releasing the counterpart. When the electromagnet is turned off the brake disk strikes against the counterpart without any braking. When the two pieces come together they produce a relatively loud noise which can be perceived as disturbing in an operating room.

Therefore another objective of the invention is that of providing a brake for the stand joints, which has lower noise with good braking properties. This objective is attained according to the invention by de-actuating the electromagnet in steps, rather than all at once in such a way that the brake disk strikes the counterpart under the force of the spring.

An improved variant provides that, instead of the spring to press on the brake disk, there is a permanent magnet which in the zero-current condition holds the brake applied. The advantage of this design over the known ones is the even better ability to control the braking process without noise and the reduction of moving parts subject to wear, namely the springs.

Another aspect of the invention concerns simplification of the parts of the stand. While conventional stands have many different parts, each of which has a particular function, the invention provides the new design of making at least the load arm and the vertical pivot arm which supports it identical, giving savings in mass production. The C-shaped cross section of these parts gives a correspondingly large free working zone for the user. The new geometry has also proved to be advantageous for the ability to balance. Other identical parts are referred to in the figures.

The most important, though not all of, the different and essentially independent inventive steps, applicable individually or in combination, aside from further different inventive improvements and variants in this patent application, can be summarized as a) Separating the two balancing functions into vertical and horizontal balancing, which can be established basically independently of each other;
b) Separation of the two functions in two different parallel planes;
c) Moving the balancing weights to a part of the stand below the center of gravity by means of parallelogram links;
d) Electrical or electronic, particularly, quantitative, measurement and adjustment of the imbalance weight on the horizontal arms or on the parts connected with them;
e) Computer-based adjustment of the vertical balancing weight after measurement of the required shift of the horizontal balancing weight;
f) Changing the stand geometry to move the center of gravity or the weight balance over a vertical pivot axis; and
g) Better selection of materials.

DESCRIPTION USING FIGURES

The figures will be described together. The description with figures and the reference symbol list make up a unit which supplement each other through the remainder of the description and the claims, in the sense of a complete disclosure. The same reference symbols indicate the same parts. Same reference symbols with different indices indicate similar parts with the same function. The figures are only examples, and they are not necessarily in correct proportion.

Figure 1:
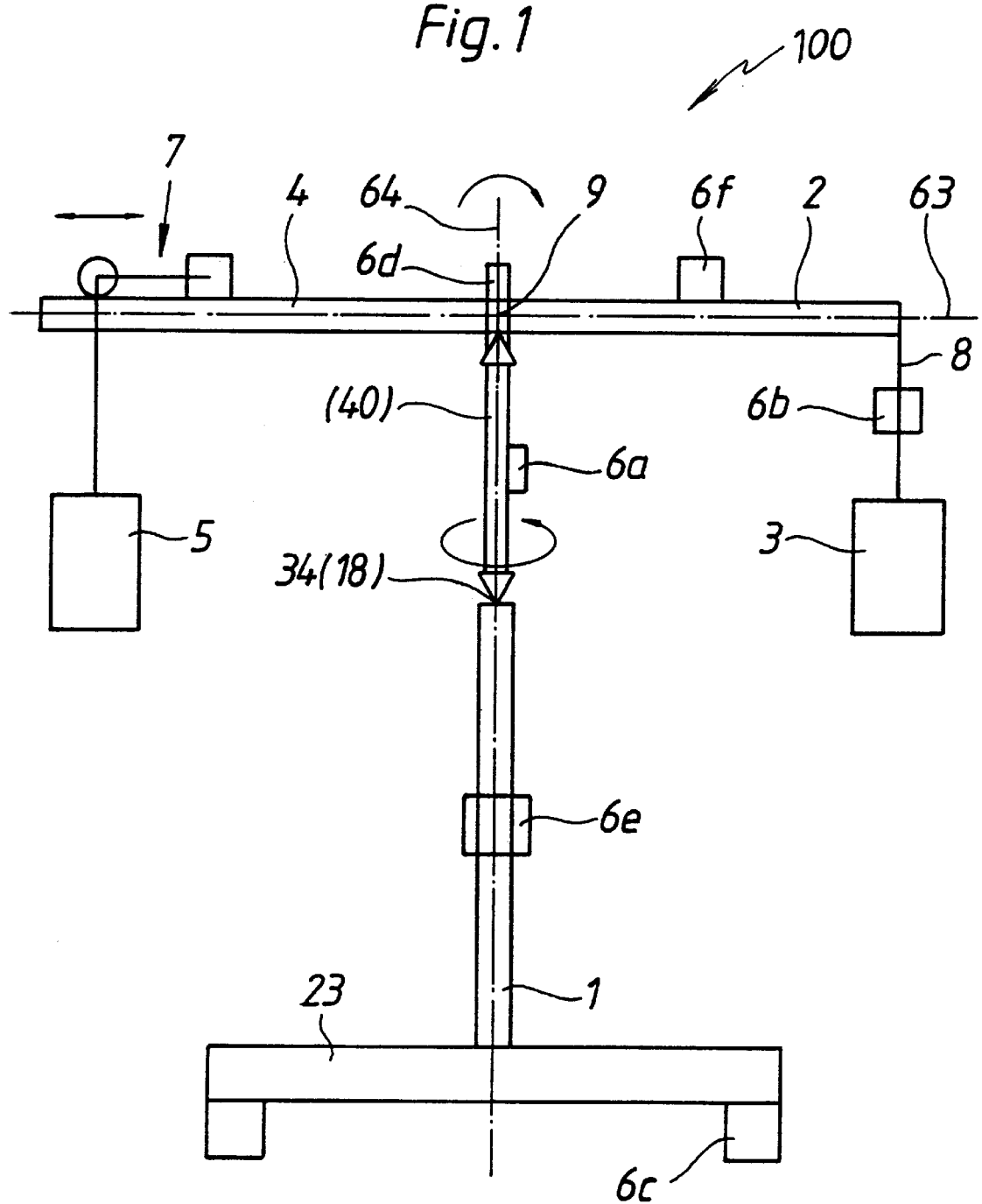

The figures show:

FIG. 1: a simplified functional sketch of a stand in which the load arm can be pivoted horizontally.

FIG. 2: simplified sketch of a stand with separate horizontal and vertical pivoting actions.

Figure 3:
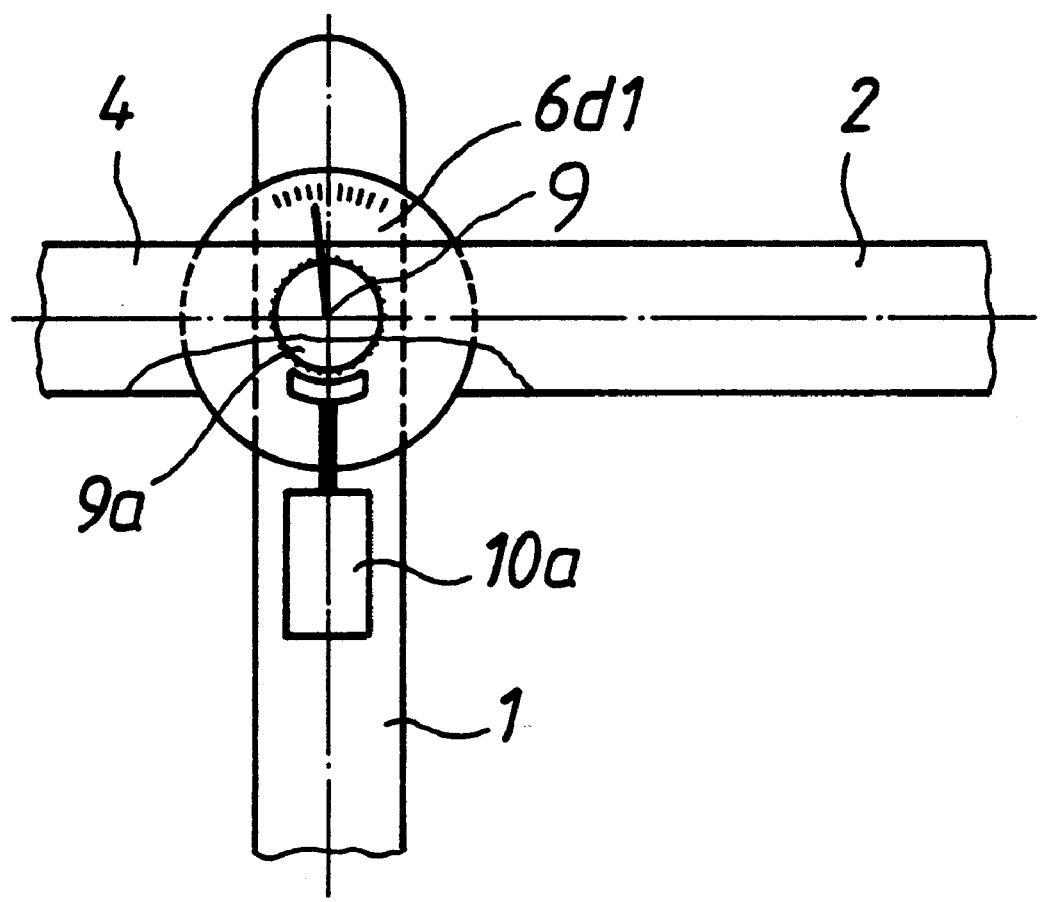

FIG. 3: a detail of a variant of a design as shown in FIG. 1 with torque measurement between the load arm and pedestal.

Figure 4:
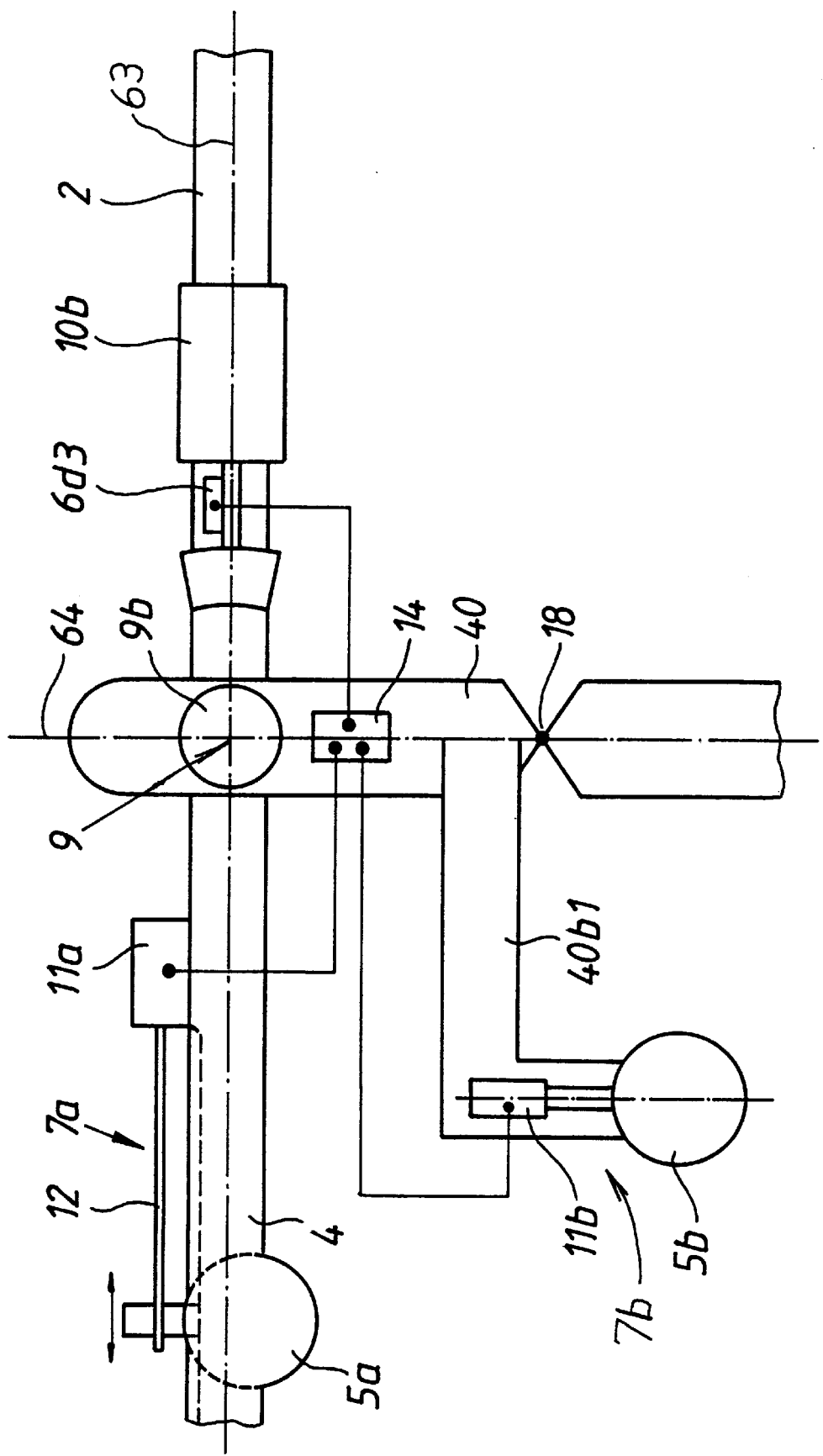

FIG. 4: a design with automatically adjustable balancing weights corresponding to the principle of FIG. 2.

Figure 5:
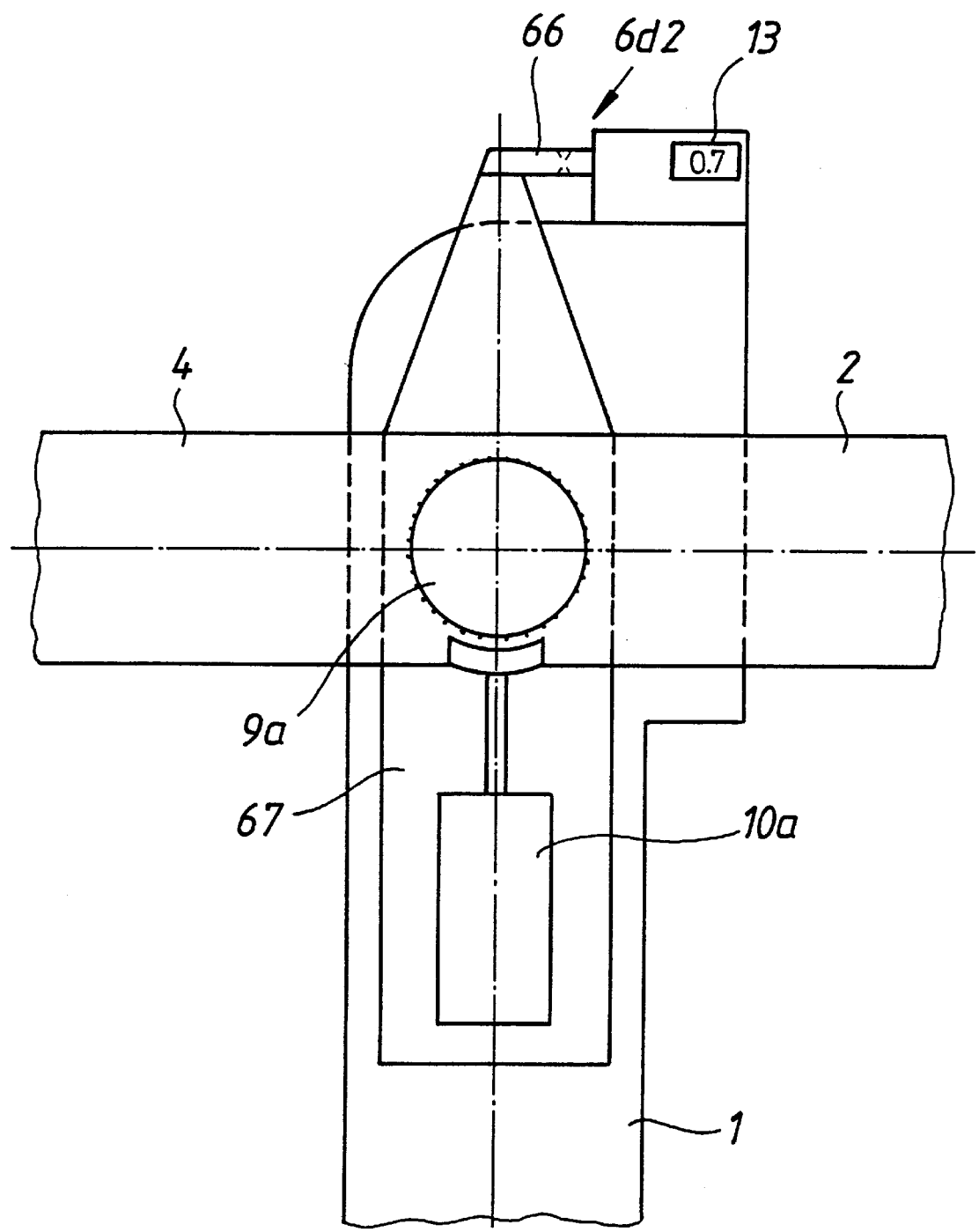

FIG. 5: a variant of FIG. 3.

Figure 6:
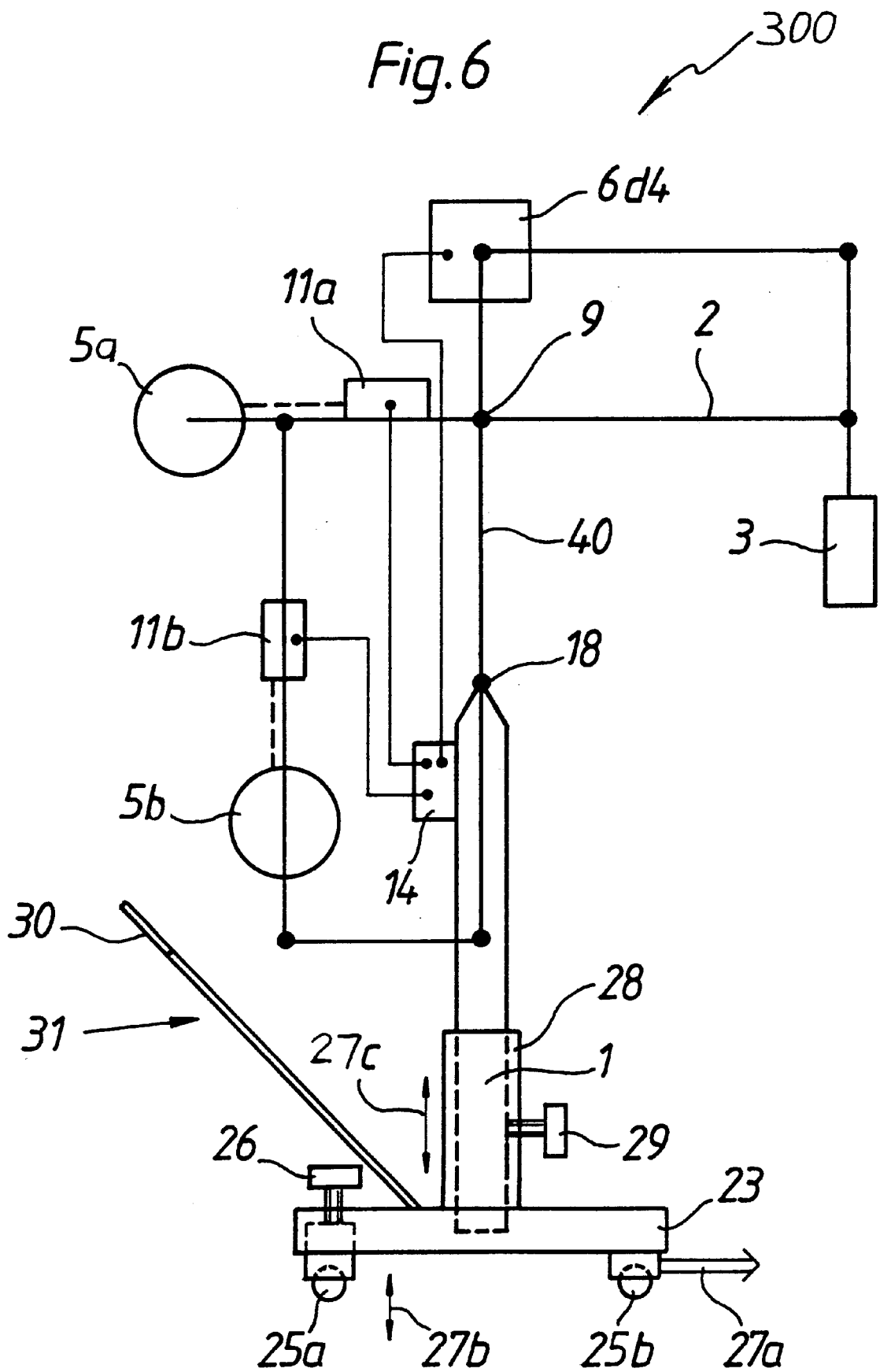

FIG. 6: a variant of FIG. 4 with parallel control elements.

Figure 7:
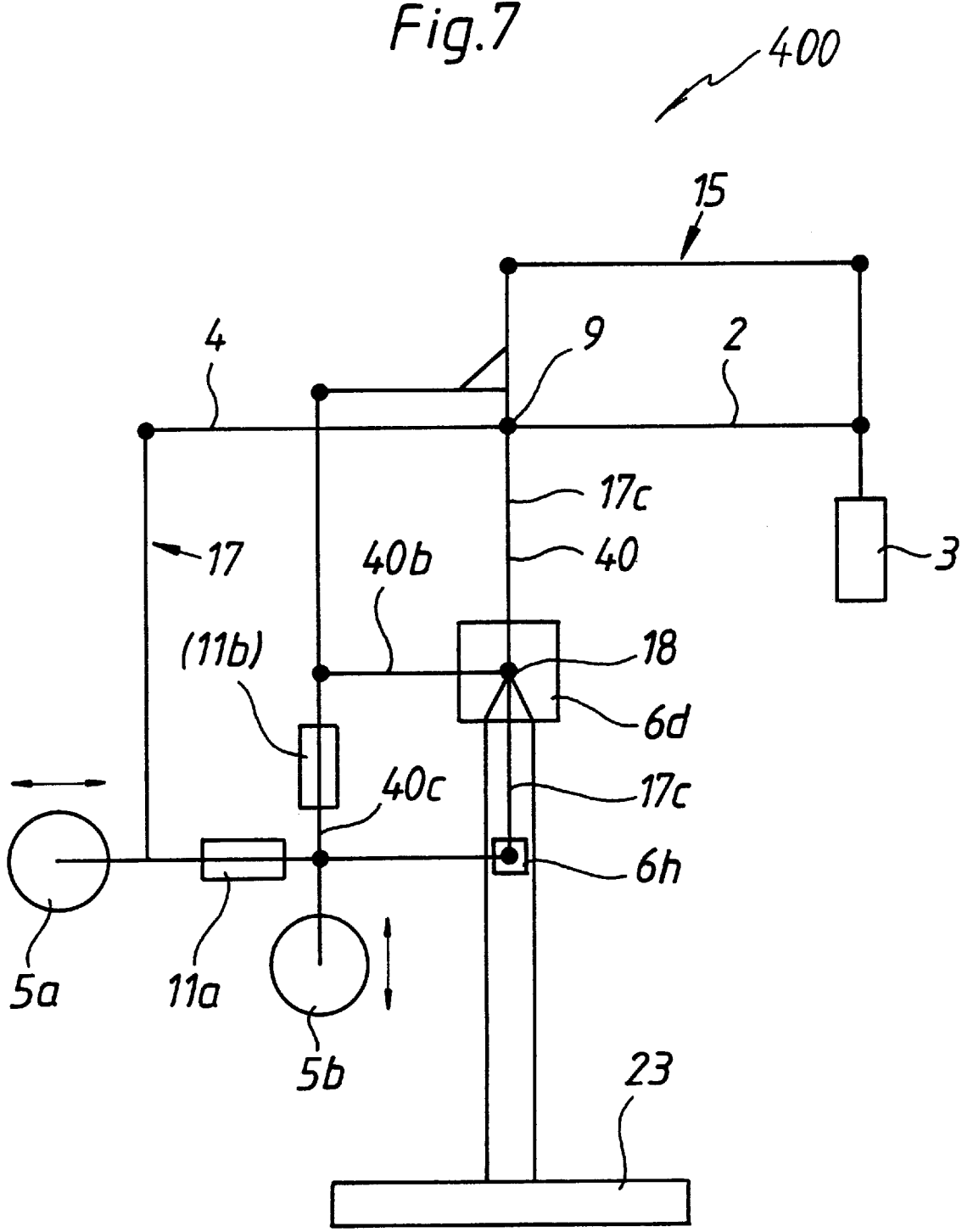

FIG. 7: a variant of FIG. 6.

Figure 8:
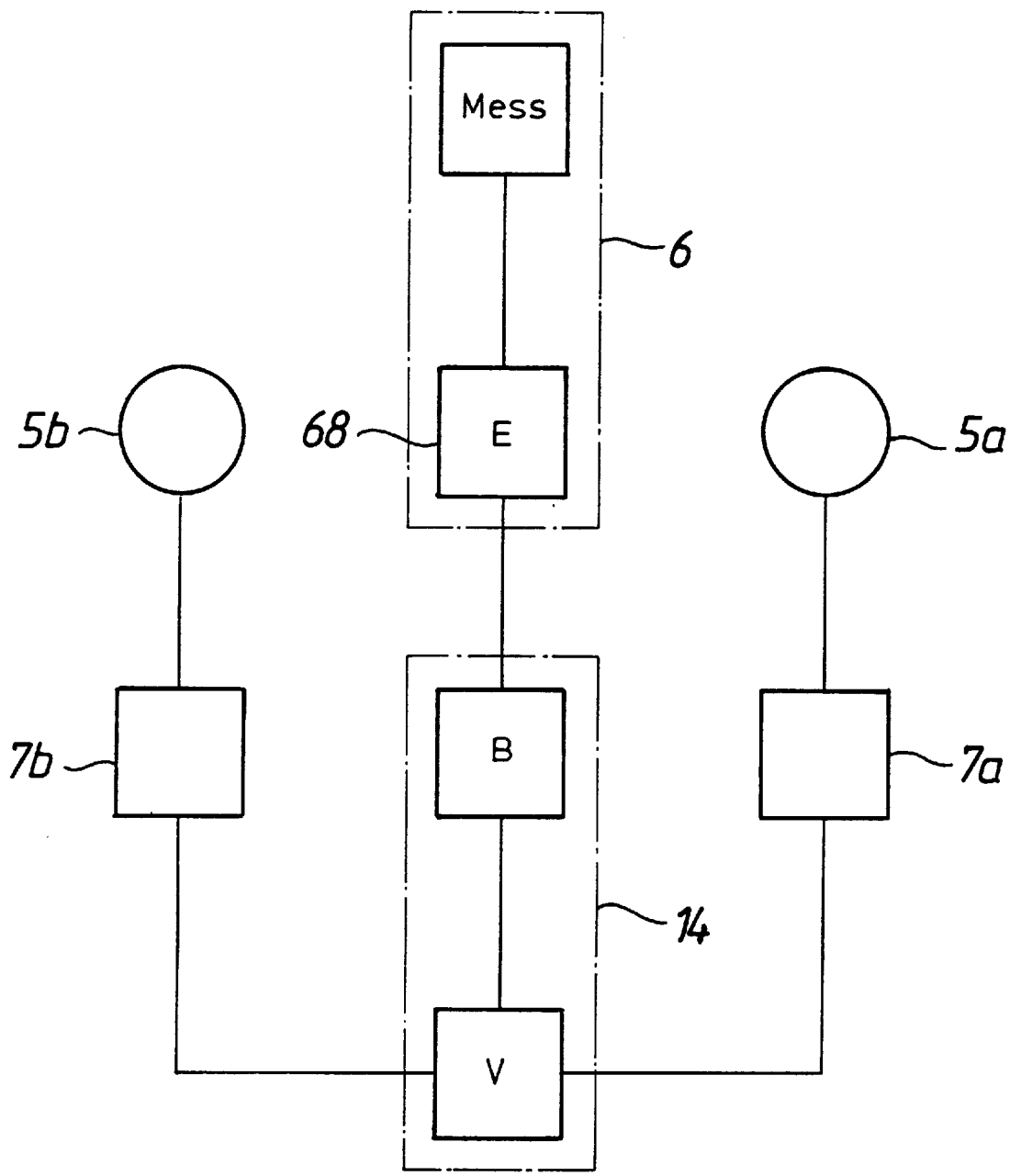

FIG. 8: a simplified circuit diagram for measurement and control of two separate balancing weights according to the invention.

Figure 9:
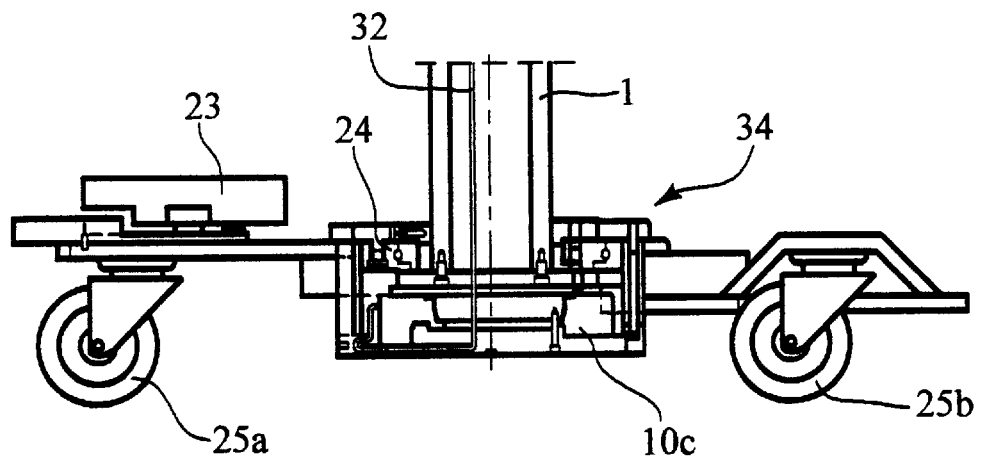

FIG. 9: The base or foot of a stand according to the invention with the new type of rotary bearing.

Figure 10:
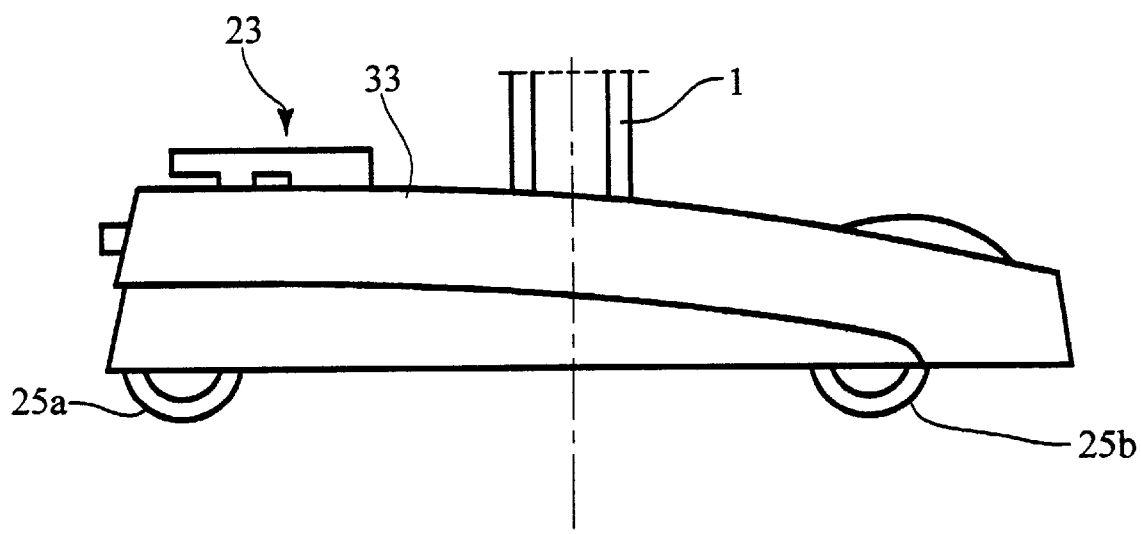

FIG. 10: The foot according to FIG. 9 with its cover.

Figure 11:
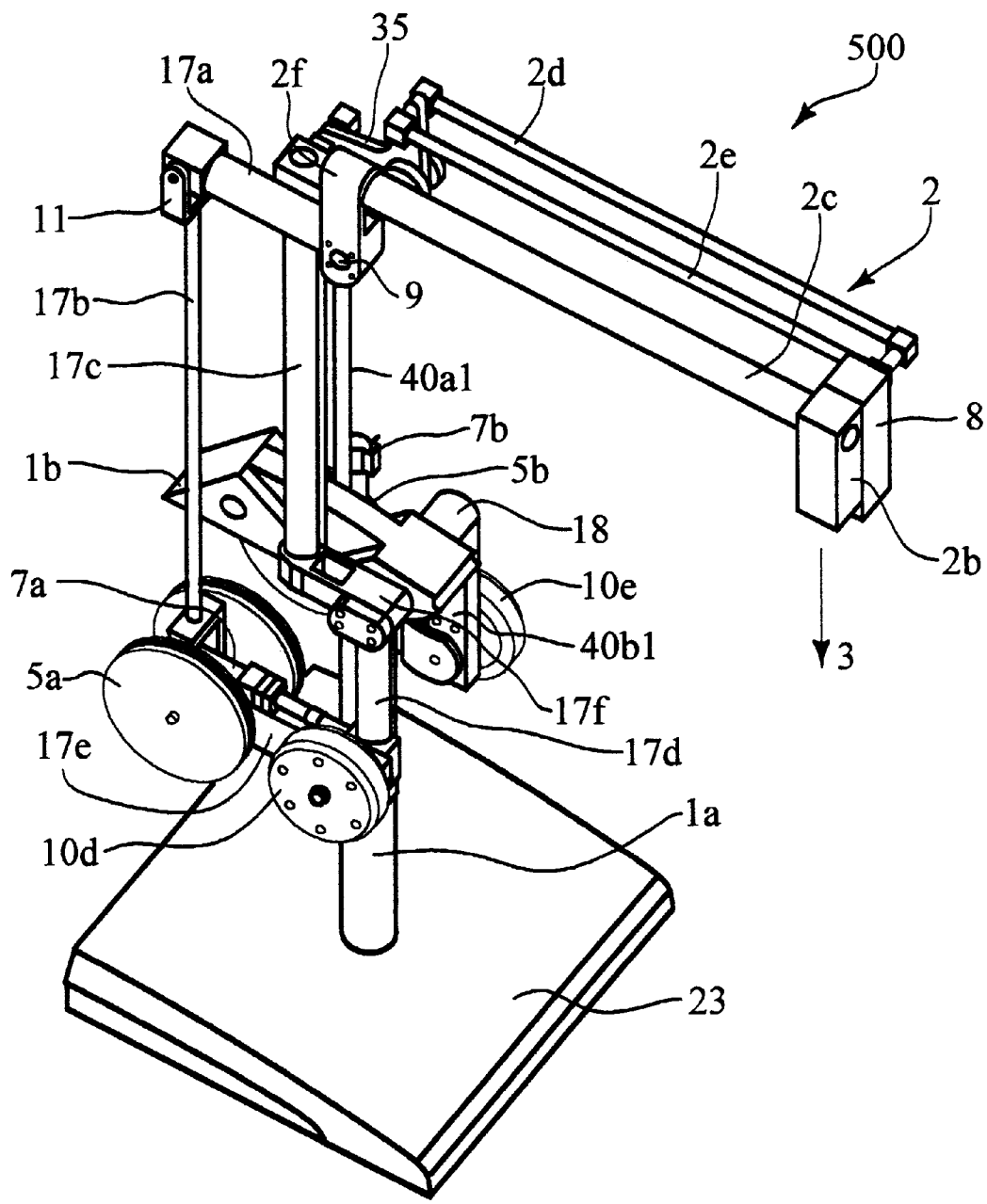

FIG. 11: An oblique view of one preferred embodiment of the invention.

Figure 12:
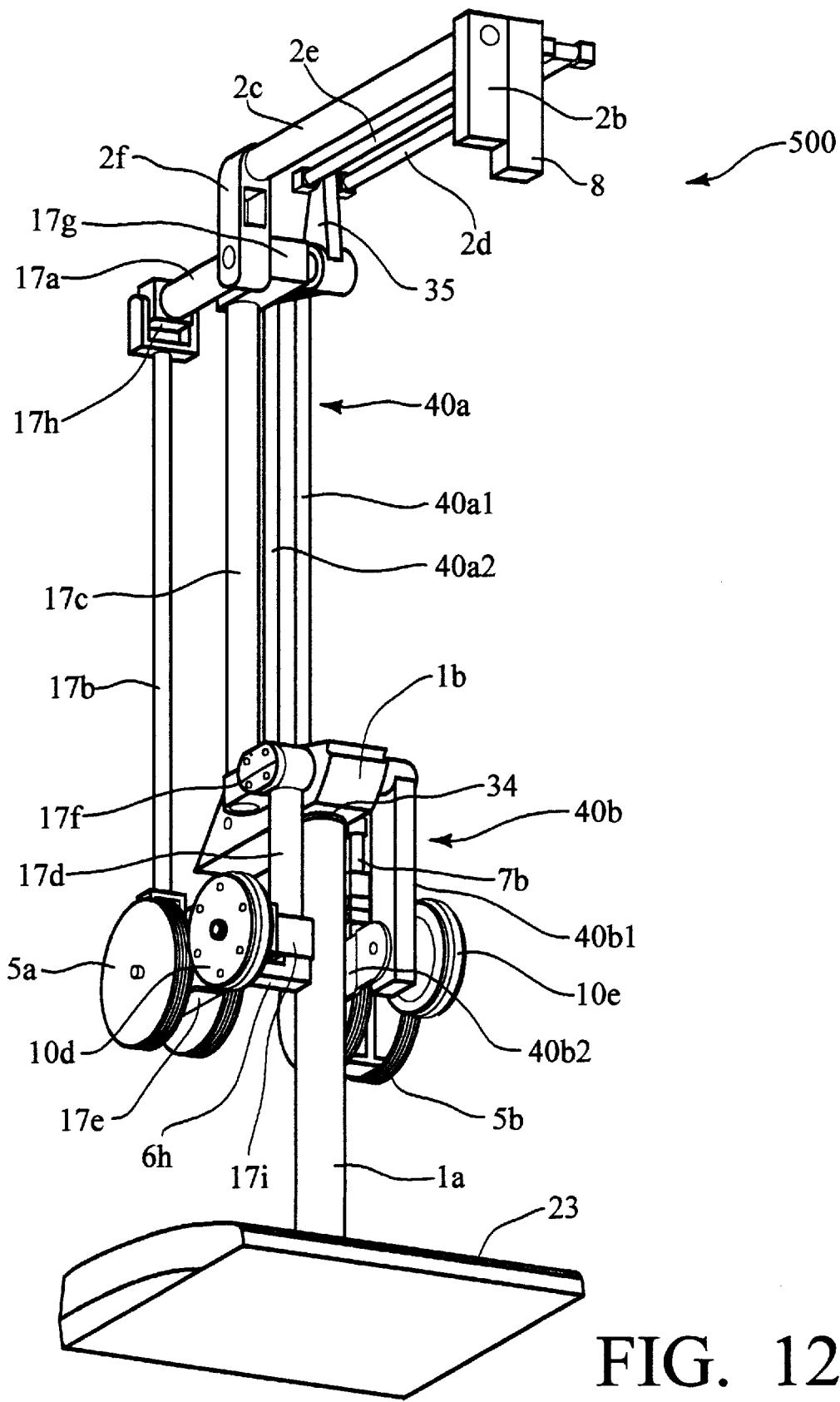

FIG. 12: The same embodiment as in FIG. 11 from another point of view.

FIGS. 13 and 14: Side views of the constructions shown in FIGS. 11 and 12.

Figure 15:
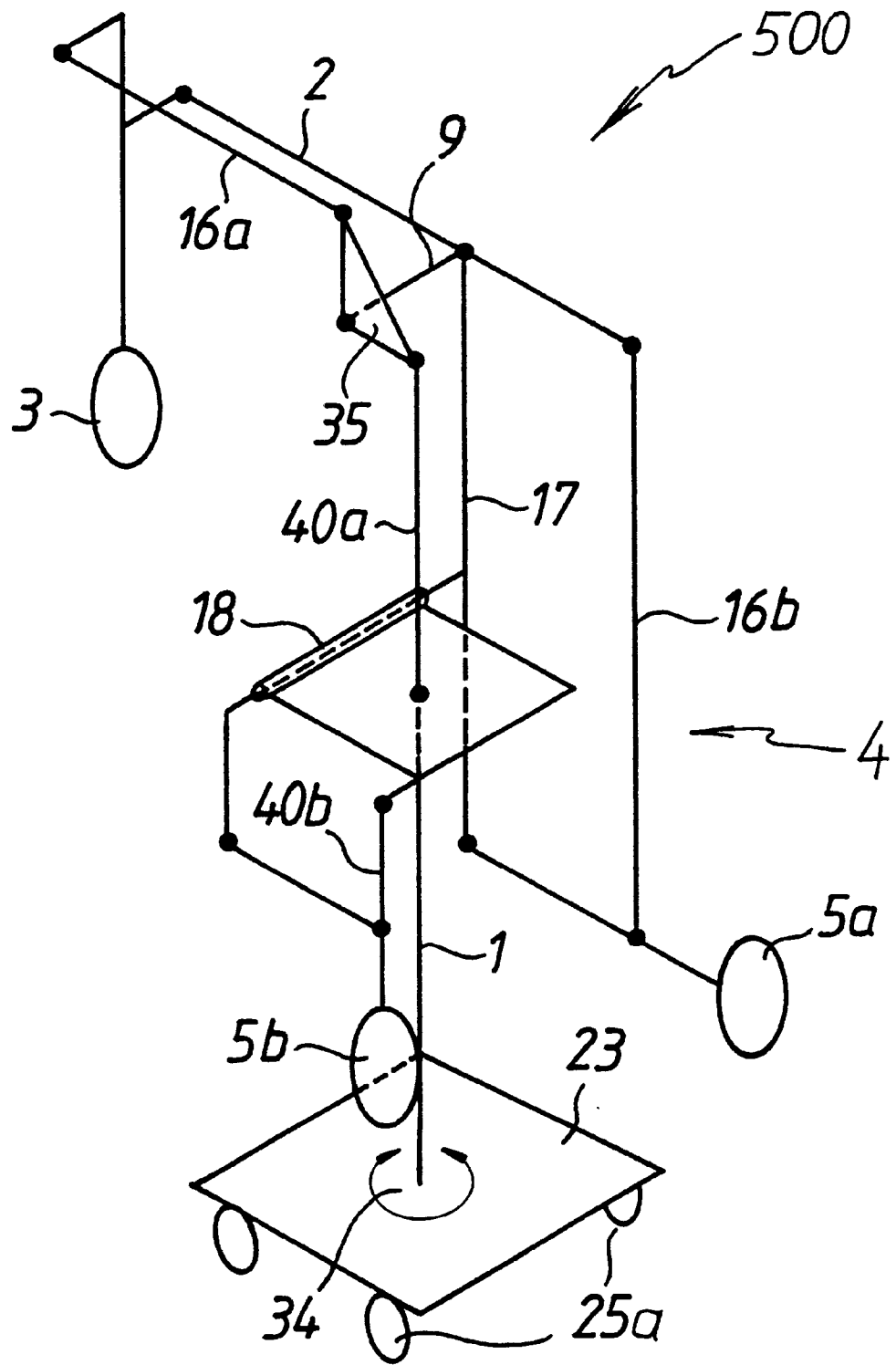

FIG. 15: A simplified sketch of the functioning of the preferred embodiment as shown in FIGS. 11 to 14.

Figure 16:
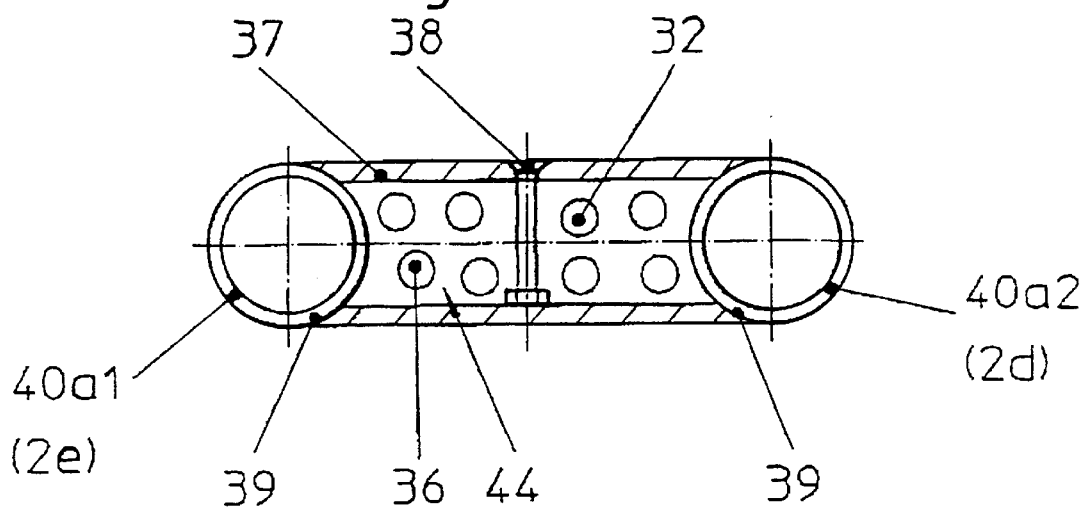

FIG. 16: A detail with the cable channel according to the invention.

Figure 17:
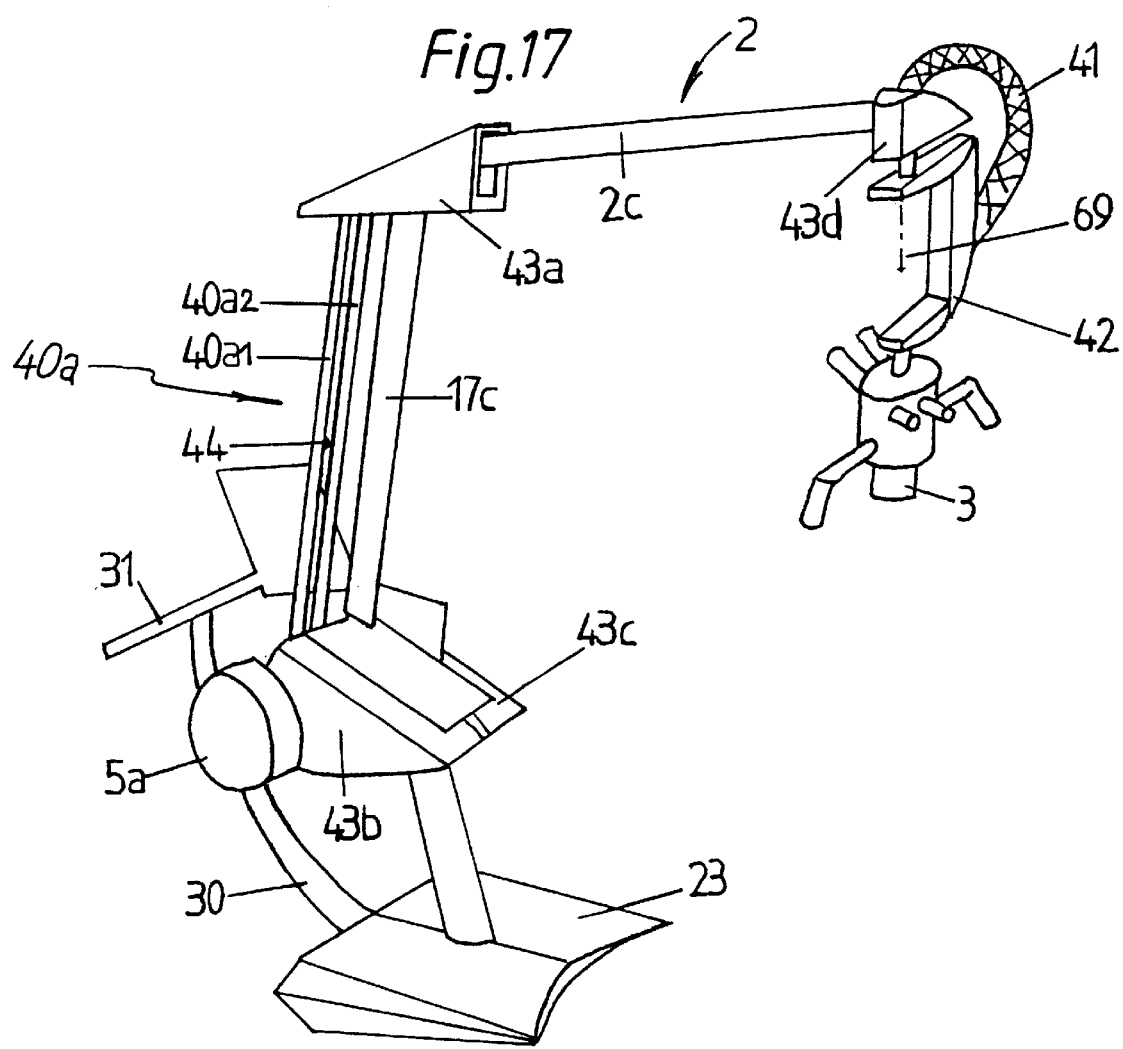

FIG. 17: A view of a stand equipped according to the invention and ready for use.

Figure 18:
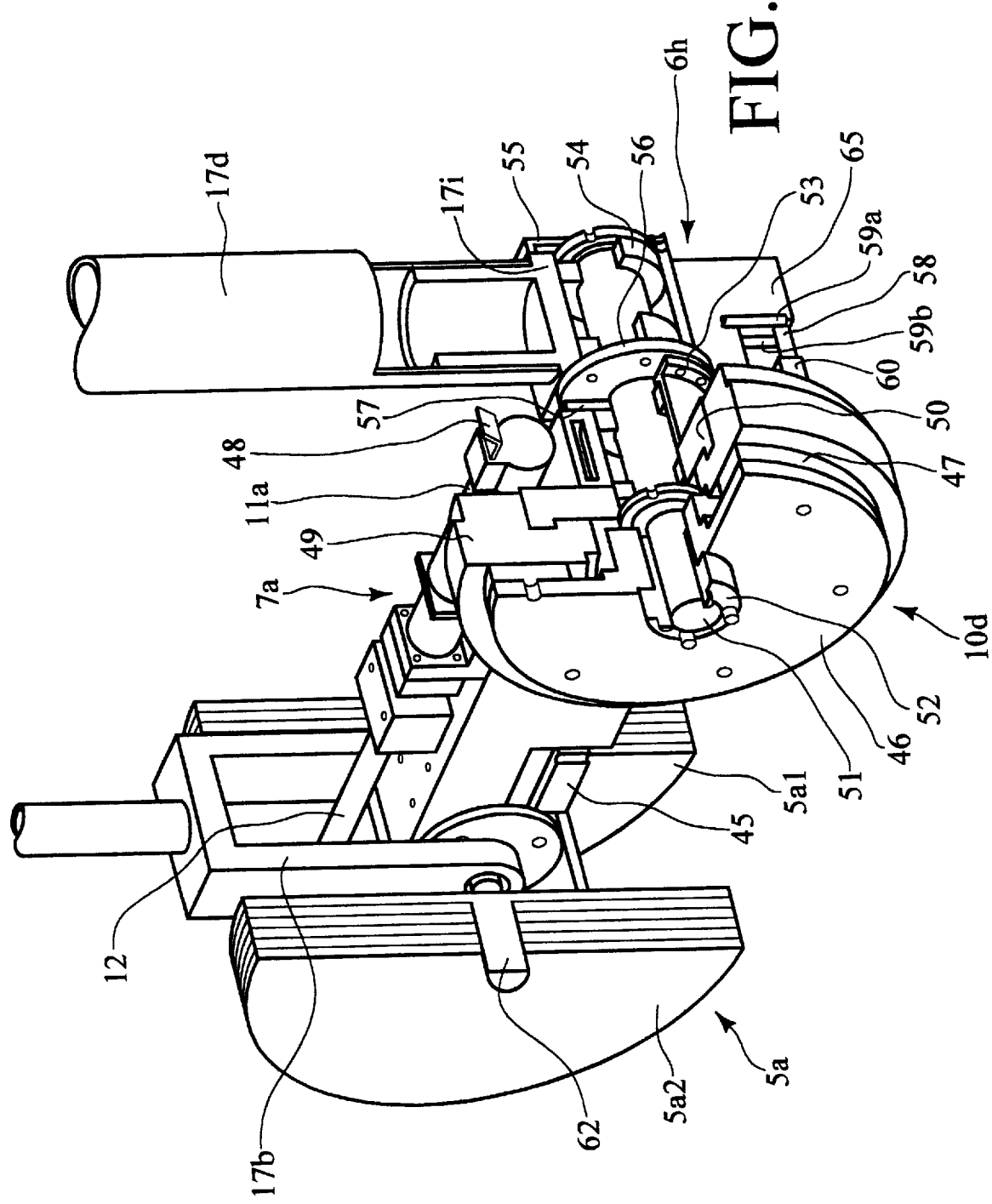
Figure 19:
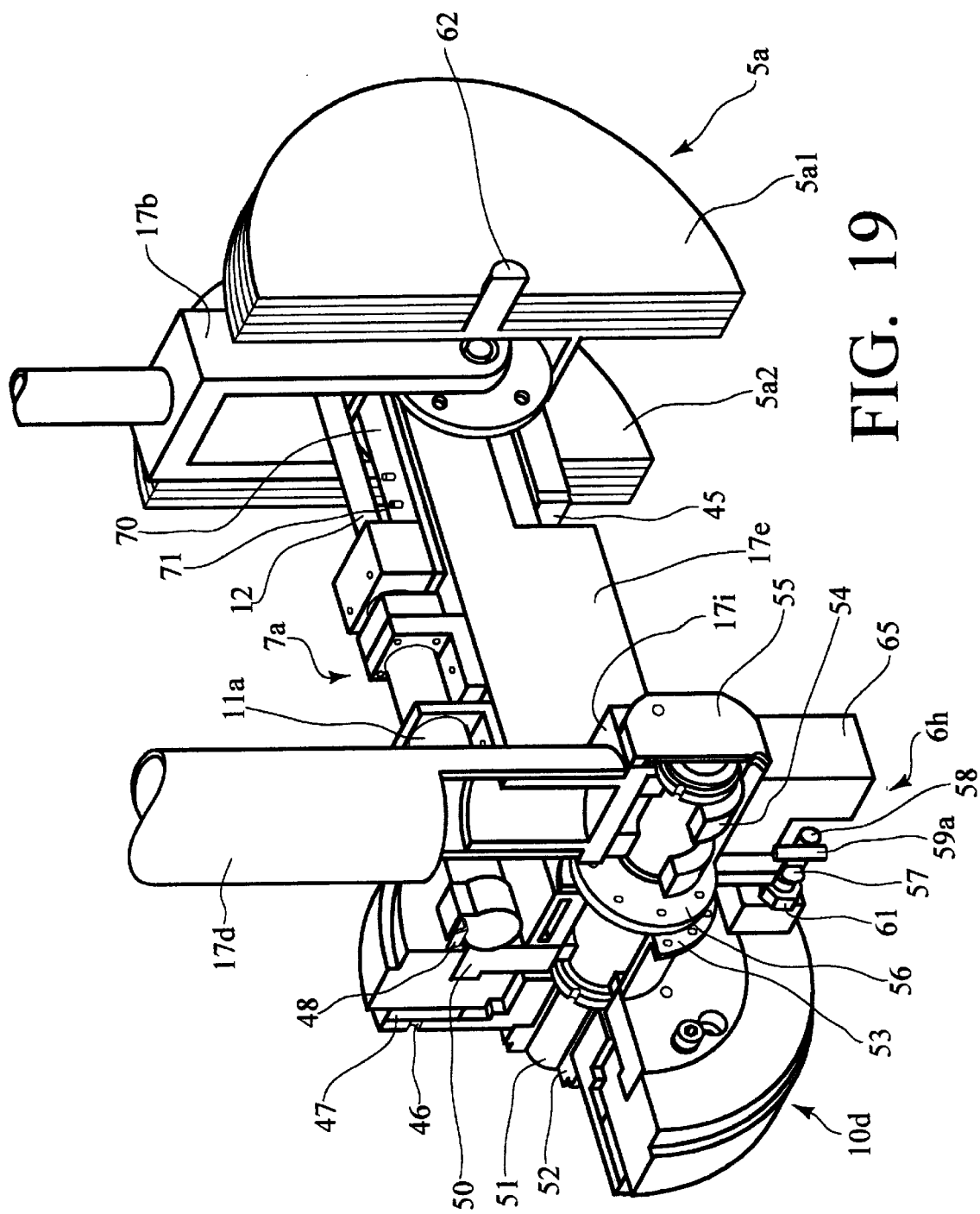

FIGS. 18 and 19: Two different views of a detail of the preferred solution according to the invention, as shown in FIGS. 11 to 14, in the vicinity of a brake and a measuring system for measuring torques resulting from an imbalance.

Figure 20:
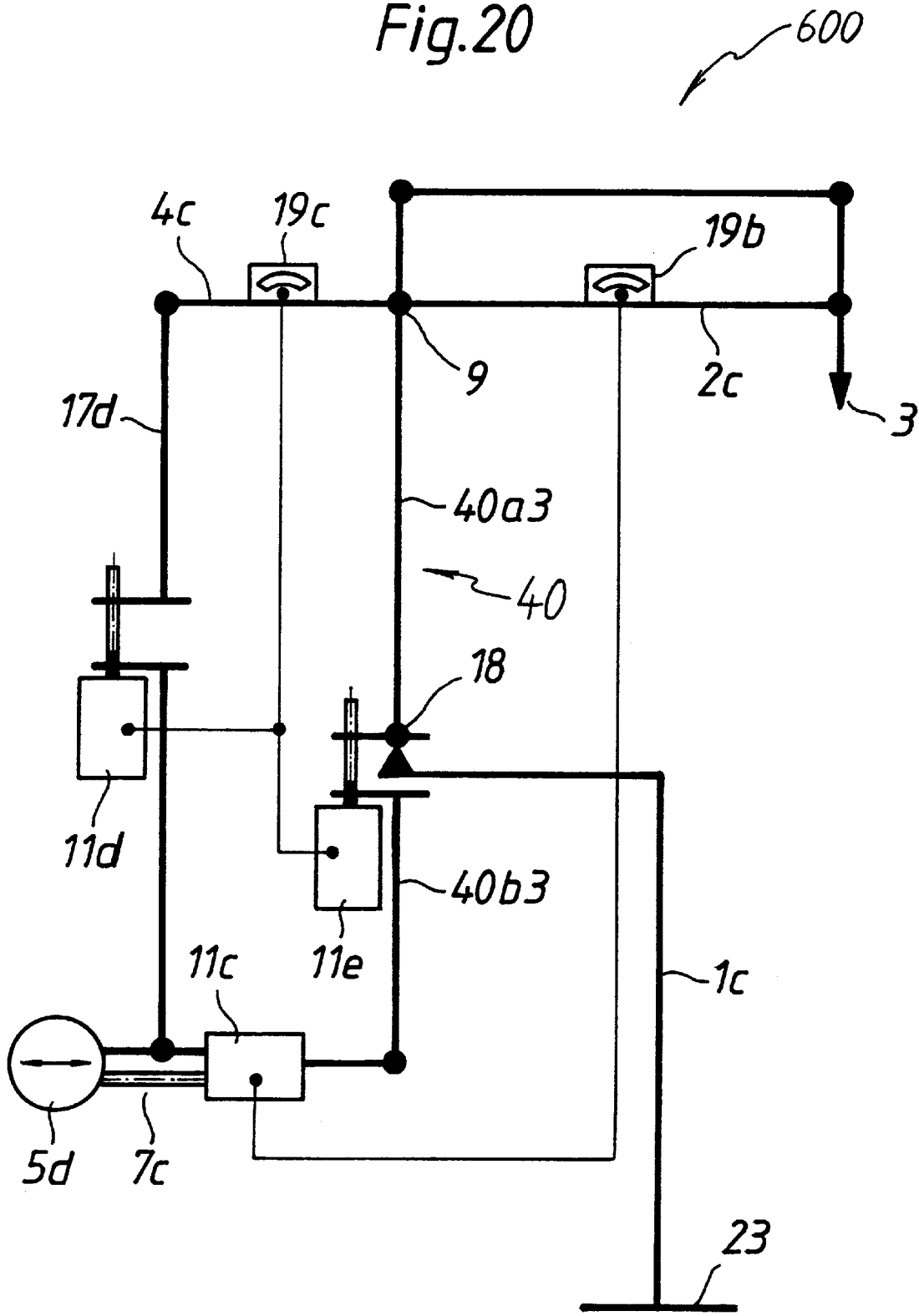

FIG. 20: A design with only one balancing weight but with a means for changing the arm geometry to adjust the balance across the vertical pivot bearing 18.

The stand designed like a wagon as shown in FIG. 1 has a pivot axis 9 across which a load and balancing arm can be pivoted out of a horizontal plane 63. A balancing weight 5, which can be moved by an adjusting means 7 attempts to balance a load 3 across the axis 9. According to the invention, adjusting means 7 is controlled by measurements which can be obtained by the measuring means 6*a–f*. These are measuring means which measure, depending on the location and nature of their mounting, bending (6*a,e,f*), tensions or pressures (6*b, c,* or *e*) or torques (6*d*) and transmit the measurements to the adjusting means.

As long as the adjusting means is appropriately controlled, e.g., computer-controlled, any of the measurements mentioned can be used to determine any weight changes of the load 3 at the load attachment 8 and to move the balancing weight 5 correspondingly. If tensions, pressures, or bends are measured in load arm 2, additional data are required to control the adjusting mechanism 7 properly. These data can, for example, be: knowledge of the balanced position of the balancing weight 5 before the change in load.

Measurements of bending moments in the vicinity of the pedestal 6*a,e* do not require supplemental information if the movement of the balancing weight 5 need only be done so that the bending moments approach zero.

The same criterion applies to a torque measurement (6*d*) in the vicinity of the pivot between the load arm 2 and the pedestal 1. The load and balancing arm, 2, 4 pivots about a vertical axis at a pivot bearing 34. A vertical pivot axis 18 is indicated at the position of the pivot bearing 34). It is advantageous, to increase the radius of action for the load arm, for the pedestal to be in two parts, being itself bendable about a vertical pivot axis 18. That is not necessarily required, though, for other variants and details of the invention.

If the upper part of the pedestal 40 can be pivoted, it is called a pivoted pedestal in the following. In FIG. 1 one can consider the ability to bend between the pedestal 1 and the pivoted pedestal 40 as produced by spring tension or the like, so that the pivoted pedestal 40 is held in its desired position at an angle to the vertical, or out of a vertical plane 64, by a spring, not shown, in the inside of the pedestal 1.

A preferred variant is shown for comparison in FIG. 2, where a pivoted pedestal 40 is mounted so that it can pivot freely on pedestal 1 about a vertical pivot bearing 18. Here one part 40*a* acts as the load part, carrying the horizontal pivot bearing 9 and the load and balance arm 2*a*, 4*a*, and a balancing arm 40*b* carrying a balancing weight 5*b* which holds the pivoted pedestal 40 above the vertical pivot bearing 18 in balance with the balancing weight 5*a,* the load, and the weight of arms 2*a* and 4*a*.

This stand, shown symbolically, presents the mechanically separated functions of horizontally and vertically pivoting about the horizontal and vertical planes 63 and 64.

The detail presented in FIG. 3 shows a pivot bearing 9a, which essentially allows the load arm 2 to pivot freely in relation to the pedestal 1. On the pedestal 1, though, there is a brake 10a which, in its braking state blocks bearing 9A and prevents pivoting. In case of imbalance at bearing 9a due to the load 3 being too heavy, a torque moment appears there and can, as indicated symbolically, be measured. As a variation of that, the measuring means 6d1 also shows an angle-measuring means, which can be used for alternative methods of measurement. For instance, if the angle between the load arm 2 and the pedestal 1, and the pressure in a measuring means 6c (FIG. 1) are measured, then the magnitude of the load or the change in the load can be determined and the balancing weight 5 can be adjusted appropriately.

The variant shown in FIG. 4 relates to a basic structure as shown in FIG. 2, which can be pivoted in both the horizontal and vertical planes. In this embodiment the pivoted pedestal 40 is firmly connected to an angular extension 40b1 which carries a balancing weight 5b. The pivoted pedestal 40 can be pivoted out of the vertical plane 64, in which case the balancing weight 5b balances the parts carried on pivoted pedestal 40. In the variant of FIG. 4 the measuring means 6d3 measures a bending moment at a bending bar or braking means 10b. A computer 14 shown symbolically evaluates the measurement from 6d3 and controls both a drive 11a for the moving means 7a on balancing arm 4 and drive 11b on balancing arm 40b1. Depending on the geometry selected for the arm, there is a relation between the required position of the balancing weight 5a and the required position of the balancing weight 5b. According to the invention, this relation is taken into consideration in computer 14 so that a single measurement in connection with the balance over the horizontal pivot plane also suffices to carry out automatic balancing, according to the invention, of pivot movements out of the vertical pivot plane.

FIG. 5 shows a variant of FIG. 3, where a bending beam 66 of a measuring means 6d2 is loaded in bending as soon as the brake 10a, which is mounted on a carrier 67, brakes it on the shaft 9a. A display 13 from which the imbalance can be read, is shown symbolically. There are also variants within the limits of the invention in which the information about the imbalance is provided to the operator visually or acoustically so as to make manual balancing possible.

The symbolic design of FIG. 6 uses parallelogram control arms, which are themselves known, for static transfer of the loads or forces and balancing forces.

The design here differs from the symbolic variant of FIG. 2 in that the balancing weights are not completely separated, particularly because the balancing weights 5b and 5c can only be pivoted simultaneously about the vertical pivot axis 18 and about the horizontal pivot axis 9.

The principle of attaching the weights in the form shown is essentially already known and not preferred. In any case, the control, according to the invention, of the two drives 11a and 11b, and the measurement by means of the measuring means 6d4 are new. FIG. 6 also shoes a particular detail, according to the invention, in the vicinity of the foot 23: Transport handle 30 with a handlebar 31 makes it possible to move the stand in a preferred direction as shown by arrow 27a. Furthermore, arrow 27b symbolizes that the wheel 25a can be raised or lowered in relation to the foot 23 (positioning mechanism 26 shown symbolically) to make transport easier. Raising the wheel 25a causes the stand to tilt slightly backward, so that it can be held and moved well by the operator. The tilt also reduces the height somewhat, as long as the load arm 2 is pivoted down.

The possibility, shown symbolically, of lowering the pedestal 1e in relation to a shell 28, which is rigidly connected to the foot 23, also makes transport easier (arrow 27c). A locking knob 29, shown symbolically, allows locking in the desired vertical position. Lowering the pedestal 1e not only reduces the height, but also lowers the center of gravity of the stand, giving more safety during transportation.

The variant of FIG. 7 corresponds to the simplified sketch of FIG. 2 to the extent that the vertical and horizontal pivoting movements are completely separated. The pivoted pedestal 40 with its balancing arm 40b carries the balancing weight 5b, which is possible only about the vertical pivot axis 19 together with a corresponding pivoting movement of the pivoted pedestal 40. On the contrary, the load arm 2 and the balancing arm 4 or the parallelogram control 15 or 17 connected to it are shaped so that pivoting of 15 and 17 is possible about the horizontal pivot bearing 9, independent of the pivoted pedestal 40. Part of the parallelogram 17 in the figure coincides with part 40a.

The measuring possibilities provided in this example are examples and are shown as alternatives with measuring means 6d or 6h.

Such a structure would fall within the limits of the invention even without measuring means and with purely manual movement.

The new and inventive moving method is shown symbolically in the block circuit diagram of FIG. 8: A measuring means 6, which may include a position-determining means 68, measures the imbalance parameters. The measurements are sent to a control 14 which carries out computations and provides positioning commands. The position of balancing weight 5a is adjusted directly by an adjusting means 7a. The adjustment value producing that adjustment is computed in the control 14 by means of tables or formulas to give an adjustment value for the balancing weight 5b, which is accomplished by the balancing means 7b.

The particular and inventive novelty in the subject of FIG. 9 is, among other things, the use of a crossed roller bearing 25 to mount the pedestal 1 in the foot 23. The transverse roller bearing 24 thus forms the rotary bearing 34 making it possible to rotate the stand about a vertical axis.

Wheels 25a and 25b are shown as pivoting wheels. It is preferred, though, that only one wheel or one pair of wheels be pivotable about a vertical axis, while another wheel or another pair of wheels is fixed in the sense of a preferred direction of movement.

A braking means 10c in the vicinity of the rotary bearing 34 is provided to prevent undesired rotation about a vertical axis. The braking means can be released automatically through a power line 32.

FIG. 10 shows a housing 33 for the foot 23.

FIGS. 11 to 14 show a preferred embodiment of the invention with many identical parts, which act against rational production according to the invention. A parallelogram guide 17 with individually labeled parts 17a–f carries the balancing weight 5a and a measuring means 6h. A pivoting pedestal 40 with the parallelogram guide 40b carries the balancing weight 5. A bearing bracket 35 and the arms 2d and e connected to it, as well as 40a1 and 40a2 assure the vertical position of the load mount 8 for all pivoting movements.

At least some of the following parts are identical to simplify production.

17a corresponds to 17d, 17g to 2b, 17c to 2c, 17f to 2f, 17h to 17i, 2e to 2d, and 5a to 5b.

A pivoting head 1b, which sits on a rotary bearing 34 on the pedestal 1a as the principal load-bearing part, holds the two pivoting stand arms 40a1 and 40a2 in position by means of an axle that is not visible. 40a1 and 40a2 could also be designed as a single piece, just as the two arm parts 2d and 2e. They are divided into two parts according to the invention, though, to reduce the height and to provide a new cable channel according to the invention.

This cable channel can be seen in cross-section in FIG. 16. It has basically a cover 36 and a cap 37, which cover the space between the two tubular arms, making a channel.

The range of the invention includes several variants for the cover 36 and cap 37, including those with snap fitting to snap onto the two tubes.

FIG. 15 shows symbolically one of the principles of the invention, which is also realized in objectives 11 to 14.

The stand according to FIG. 17 is designed in principle according to FIGS. 11 to 14. According to the invention, though, here the bends, or joints, of the stand are covered by covers, especially covers made of integral polyurethane foam. As a further novelty, the tube channel 41 is shown. It is preferably a corrugated tube in the extension of the cable channel between the arms 2 or 40a, which protects the cable which must run to the load 3 (microscope). The tube channel 41 preferably projects perpendicularly out of the plane containing the arms 2. That makes it possible for the load to rotate freely about a vertical pivot axis 69. Thus the load can conveniently be rotated in any desired direction without the cable or the tube channel 41 being in the way. It is also preferable according to the invention for air to be drawn through the tube channel 41. The air flow can be used for cooling, or to evacuate the volume below a drape. If desired, such a suction process can be continued through the cable canal between the arms or through the arms themselves.

The braking and measuring means corresponding to the detail drawing in FIGS. 18 and 19, or the adjusting mechanism 7a for the weight 5a functions as follows: in the unpowered state of the electromagnets 50 the braking disk 46 is attracted by the permanent magnet 49 through the brake grips 47 and the brake is applied. The brake disk 46 is rigidly mounted to a shaft 51 by means of a clamping collar 52. The permanent magnet and electromagnet are connected firmly to it by means of a bearing shell 53 which is bolted to arm 17e. Pivoting of the arm 17d is basically possible through the bearing 54b. However, a rotation-sensing disk 56 is firmly connected to the shaft 51 between part 17i and the bearing shell 53. It carries a solidly mounted rotating carrier 57 which projects downward and fastens to a bending bar by means of mounting nut 61. The bending bar 58 is held between two stops 59. The stops 59 are firmly mounted in a measuring body 65 of the measuring means 6h. The latter is shown in cross section for clarity. The measuring body 65 is solidly connected to part 17i and thus to part 17d. Thus its pivoting on its bearing 54 can be neglected.

However, a tendency to pivot leads to a bending load on the bending bar 58. Strain gauges (60) are mounted on that bar. They modulate electrical voltage pulses to provide a measurement for the corresponding control.

Obviously other measuring elements such as, for instance, piezoelements or the like, in forms which are themselves known, can replace the strain gauges and bending bar shown for example in the variant presented.

According to the invention, one preferred measurement and control routine makes it possible to control the balancing weights at different speeds. For instance, with voltages between plus and minus 10 volts, the command for a fast adjustment can be issued. At plus or minus 5 volts, on the other hand, a standard adjustment rate is specified; and in the region between plus and minus 2 volts, slow movement to the desired adjustment of the balancing weight is specified following a voltage ramp. Likewise, variants within the computer control system 14 are conceivable, with waiting periods between the latest measurement results and the latest adjustment processes. As a general rule the measurement is done with the brakes applied. Released brakes make it possible for an operator to change the position of the stand.

One special embodiment of the invention also provides absolute position measurements of the balancing weights 5a, or at least one of them relative to its carrier arm (17e), aside from force measurements. An optical or magnetic bar code 70 is read by a magnetic or optical sensor element 71. The sensor element is connected, directly or indirectly, to the balancing weight 5a, so that its position on arm 17e can be determined. Absolute position measurements have the advantage that they can, according to a further development of the computer control 14, be used to direct the balancing weight 5 to a certain balance position depending on load changes. Basic settings or calibrations are, accordingly, also possible. Thus, for instance, when an added part is mounted to the load (load increase), the approximate weight of this part can be entered in the control unit, so that the control unit can position (reposition) the balancing weight without even once performing a measurement by the measuring means 6a. One particularly simple variant is based on the factor determined from the geometry of the stand. When one of the balancing weights is moved in one direction or the other according to a measurement, the other balancing weight is moved over a distance decreased or increased by the factor. That can be accomplished by appropriately controlling the number of turns of the positioning drive or by different thread pitches of the spindles 12, etc. The design according to FIG. 20 shows an alternative which, again, results in only one balancing weight 5d. In the vertical pivoting stand shown, the load 3 can be balanced (for the horizontal pivoting motion) by adjusting 5d, as for a balance, in the unbraked condition, so that the stand is at rest across the vertical pivot axis 18.

The measurement for the purpose can be accomplished with a bubble level design 19 or the like on one of the bars which is now horizontal (e.g., 2c). Either by means of a computer not shown here, or as already me d, the lower part of arm 17d and arm 40b3 can be moved by spindle drives 11d or 11e for pivoting in the vertical plane, so as to approach the balancing weight 5d or to move away from it and from the vertical pivot bearing 18. Thus balancing for the vertical pivoting motion is attainable, so that equilibrium is maintained even with the arms 40a/b or 17d positioned obliquely.

Instead of using a computer to adjust the positioning drives 11d,e, by one variant a balance can be measured by a second measuring means 19c in a position tilted from the vertical so as to control the positioning drives 11d/e.

List of Reference Numbers

1a,c Stand, which can preferably roll over the floor; shown only symbolically by a straight rod; could also be C-shaped, box-shaped, or comparably designed; need not necessarily be used for floor mounting or positioning, but could also be inverted and mounted on a ceiling, other surfaces, or items of furniture, movable if desired.

1b Stand head; a part which closes the top of the stand to accept the pivoting part of the stand and, in particular, which itself sits on the pedestal 1 so that it can rotate.

2a Load arm, which can be made up of several rods; for instance, one or more parallelogram guides.

3 Load, such as a microscope; could also be any desired part that must be held on a stand, such as a robot arm, telescope, or the like.

4a Balancing arm, which can be constructed of several rods; e. g., one or more parallelogram guides.

5a–d Movable balancing weight; can be in one piece or, especially, divided. One of the different aspects of the invention is that two separate balancing weights swing for two balancing functions with separate movements, namely, about a vertical and a horizontal plane (63).

6a–h Measuring means for forces, force changes, weights or weight changes on the load arm, especially for measurement of pressure, tension, bending or torsional moments at places on the stand where such measurements can be picked off directly or indirectly.

7a–c Means for moving a balancing weight; comprises, for instance, sliding or roller guides, drive belts, drive spindles, or the like, and a drive 11 as well as suitable bearings and connections.

8 Load mount; comprises means for holding a microscope or other load. In particular, the load mount according to one further development of the invention comprises its own balancing system, corresponding to the balancing system of the stand itself, with load arm and balancing arm, as well as measurement means and balancing weights.

9, Pivot axis (horizontal pivot axis) for the load arm 2 at and/or balancing arm 4, at which it could pivot out of a horizontal plane 63.

10a–e Brake mechanism for braking or mutual fixing of parts which can move with respect to each other.

11a–c Drive, preferably electrical, to move a balancing weight.

11d,e Drive to change the stand arm geometry, especially lengthening or shortening arms 17d and 40a3 or 40b3. The arms mentioned are lengthened or shortened while retaining the same shape. The parts used for that are indicated only symbolically. One skilled in the technology will find quite varied solutions such as parallel spindles or guides, telescoping connections, etc.

12 Drive spindle, preferably self-limiting, to drive a balancing weight.

13 Display, can be an ordinary pointer or an electrical display such as a CRT, LCD, LED, etc., for optional indication of measurements and movements.

14 Measurement converter, control, logic, or computer, etc., which detects, calculates and in some cases uses the measurement from the measuring means 6, perhaps based on a table, to determine the position for the balancing weight or to control drive 11 (trial and error) to position a balancing weight.

15 Parallelogram guide for the load arm; corresponds to the load arm 2 in a preferred embodiment. Also makes it possible to hold the load-holding part 8 vertical even in case of a pivoting movement across the vertical pivot axis 18 or the horizontal pivot axis 9. These are known from table lamp stands and from parallel control arms of motor vehicles.

16 Tension arm horizontal (a), vertical (b).

17 Parallelogram guide for the balancing arm 4 or for shifting the mounting of the balancing arm and of the balancing weights downward to make the center of gravity lower; corresponds to the balancing arm 4 in one preferred embodiment.

18 Pivot point or section through the axis or rotation or the pivot axis (vertical pivot axis) about which the stand can pivot out of a vertical plane.

19 Angle/tilt sensor.

19b,c Tilt sensors (spirit levels) which in the unbraked condition of the stand as shown in FIG. 20 can establish a balance across the vertical pivot bearing 18. Balance in the position shown, measured at sensor 19b for vertical arm 40, indicates good adjustment of the balancing weight 5d. If necessary, the balancing weight is readjusted by means of positioning means 7c after a change in the load 3. A positioning drive 11c acts on the weight 5d by means of a threaded rod, for instance. Adjustment for the pivoting movement out of the horizontal plane is accomplished by adjustment, according to the invention, of the lengths of arms 17d and 40a3 or 40b3 so that the center of gravity of the balancing weight 5d, or of the rods, etc., connected to it are moved down or up in relation to the vertical pivot axis 18, or are moved farther from or nearer to this bearing 18. Because of this new measure it is possible to balance out any imbalance that arises in the oblique position of arms 40a, b or 17d. that can be done permanently by continuous measurement using sensor 19c, or, as by other inventive solutions, necessarily coupled with the adjustment of the balancing weight 5d. The difference in these variants is that no separate weight is provided for the vertical pivoting balancing. Rather, he horizontal balancing weight 5d is also used for this balancing. This has the disadvantage, compared with variants having complete separation between the two balancing weights, that the balance position, once taken, functions ideally only for a single load; therefore continuous adjustment is preferred for such a design.

20 Line

21 Guide

22 Adjusting means, e.g., control knob and control system.

23 Foot of the stand, which supports it on the floor, but can also be considered for use inverted as a ceiling mount or the like, with modified mounting elements (no rollers).

24 Crossed roller bearing as a substitute for two ball or roller bearings.

25 Wheels for the foot. They can be mounted rigidly or so that they can pivot. It is preferable to have a way of making them rigid, or so that they can be lifted up from the floor, or in relation to the foot 23, or so that they can be retracted into the foot 23 so that the foot can be set down on the floor.

26 Positioning mechanism, such as a drive screw.

27a,b,c Arrows

28 Shell. The pedestal fits closely into it. It can, if desired, take on the function of a rotary bearing.

29 Locking knob to lock the telescoping movement of pedestal 1 in shell 28.

30 Transport handle to push or pull the stand. With a special handle rod 31 it preferably produces a specific transport direction (arrow 27a to the front).

31 Handlebar

32 Electrical or optical supply line or the like for functions of the stand, such as braking or the load (microscope).

33 Housing of the foot 23, for lowering the total center of gravity of the stand; of cast material or the like and/or covered or made of plastic.

34 Pivot bearing

35 Bearing bracket

36 Cover for the cable channel between the parallel arms of the stand.

37 Cap for cable channel.

38 Mounting screw to connect cover 36 and cap 37. The cover can if desired be cemented to the arms or held only by screws 38.

39 Bonding points.
40*a–c* Pivoted pedestal
40*a* Pivoted pedestal is the vertical part in the resting state, which carries the horizontal pivot bearing 9 or holds it elevated. Its function is to move the pivot bearing 9 to the side, and the load arm 2 along with it, in case of pivoting out of a vertical plane 64, so that the load 3 can be moved back and forth from the vertical plane 64. It has a vertical extension below the vertical pivot bearing 18, which serves as a balancing arm and holds the balancing weight 5*b*.
40*b* Pivoted pedestal balancing arm. The pivoted pedestal 40*a* and the pivoted pedestal balancing arm 40*b* correspond in their function to a load and balancing arm, comparable with arms 2 and 4. This is also a special point of the invention, that the balancing functions are completely separated and are reintegrated through the pivoted pedestal 40 with the horizontal bearing 9 and the vertical bearing 18.
41 Tube channel—especially a corrugated tube. It serves to hold and protect the electrical or optical supply cables for the load 3 and is a continuation of the cable channel 44 between the stand arms. In particular, it is divided into two parts along the long axis, so that it can be opened along its length to remove cables.
42 Microscope mount. It can be a conventional one, as stated for the state of the technology, but it is preferably constructed according to a new inventive principle, which is the subject of a patent application submitted on the same day is "m. Z.: R-P-3623-CH", to which reference is expressly made for purpose of combination.
43*a–d* Covering cap, preferably of closed-cell integral foam on all sides. It can be removed easily for service from the places on the stands with joints. It prevents damages or injuries in case of collisions. Another advantage which should be emphasized is its light weight and the ability to produce any desired shape. That gives the stand a pleasing appearance at low cost.
44 Cable channel
45 Slide guide for the balancing weight 5 on the balancing arm. Only one slide guide is shown for balancing weight 5*a* in the figures. It is preferable to provide an identical slide guide for the balancing weight 5*b*, which need not be shown in detail.
46 Brake disk of the brake 10.
47 Brake gripper. This is preferably a pole-piece of a magnet 49, but could also be made of a different, non-magnetic, material to achieve a different braking action against metal. If desired, it can even be just a thin coating of a pole piece of a magnet 49.
48 Electrical control connections for the positioning drive 11 of the positioning means 7 for the balancing weights 5 and/or for an electromagnet 50 of the brake 10.
49 Permanent magnet
50 Electromagnet, poled so that when activated it cancels the magnetic field of the permanent magnet 49.
51 Shaft in the brake 10. It transfers the torsional moment when brake 10 is applied.
52 Locking collar, which fastens the brake disk 46 to the shaft 51.
53 Bearing shell. It holds the ball bearing 58 on the shaft 51 in part 17*e* of the parallelogram guide 17.
54 Bearing, such as a ball, roller or needle bearing. It minimizes the friction between the parts or arms of the stand which move in relation to each other. As an effect according to the invention, it provides particularly easy manipulation of the stand with the brakes released, so that an operator is subjected to only minimal fatigue, assuming good balancing, and can position the load, especially a surgical microscope, without resistance and very precisely.
55 Hub cap to cover the stub of shaft 51 and if desired, to tighten the bearing 54*b*.
56 Rotation sensor disk, rigidly connected to shaft 51. It transmits torsional moments, by means of the rotation carrier 57, in relation to the arm 17*d* of the parallelogram guide 17, which turns freely on shaft 51.
57 Rotation carrier
58 Bending bar. It is rigidly connected to the rotation carrier by means of the nut 61 and blocked by one stop each 59*ab* on arm 17*d* and part 17*i*. The stops 58 are connected to a measuring body 65, although they could also be designed to be integral with it. They are preferably round and lie, without play, on the bending bar 58, which is preferably also round, so that relative movements between the two can occur as nearly free from friction as possible.
59*a,b* Stop
60 Strain gauges. The strain gauge is attached to the bending bar in a way which is itself known. It allows measurement of the bend in the bar under the force transmitted to it by the rotation carrier 57. The measurement is proportional to the torsional moment transferred from the brake 10*d* and the shaft 51 in relation to the arm 17*d*.
61 Nut
62 Mounting shaft
63 Horizontal plane
64 Vertical plane
65 Measuring body
66 Bending bar
67 Carrier
68 Position determination
69 Vertical axis of rotation
70 Bar code
71 Sensor element.

What is claimed is:

1. An adjustable counter-balanced stand to hold a load in a user-selected position, said stand comprising:
   a foot;
   a pedestal extending vertically from said foot, said pedestal having a lower non-tilting portion and an upper tilting portion;
   a load arm for supporting said load;
   a first pivot means for connecting said load arm to said upper tilting portion to permit said load arm to pivot about a first horizontal axis relative to said upper tilting portion;
   a second pivot means for connecting said upper tilting portion to said lower non-tilting portion to permit said upper tilting portion to pivot about a second horizontal axis relative to said lower non-tilting portion;
   a third pivot means arranged to permit at least said upper tilting portion to be rotated about a vertical axis;
   a first balancing arm paired with said load arm;
   a second balancing arm paired with said upper tilting portion;
   a first counterweight supported by said first balancing arm, said first counterweight corresponding in weight to an absolute weight of said load;
   a second counterweight supported by said second balancing arm, said second counterweight corresponding in weight to a combined absolute weight of said load arm, said first balancing arm, said load, and said first counterweight;

said first balancing arm including a first positioning means for automatically moving said first counterweight relative to said first balancing arm;

said second balancing arm including a second positioning means for automatically moving said second counterweight relative to said second balancing arm;

a measuring means for detecting imbalance due to changes in said load and generating a signal representative of said imbalance; and remote control means connected to said measuring means and to said first and second positioning means for evaluating said signal and actuating said first and second positioning means to automatically move said first and second counterweights to approximately eliminate said imbalance.

2. The stand according to claim 1, wherein said remote control means includes a memory for storing a predetermined relationship between balancing positions of said first and second counterweights depending upon geometry of said stand.

3. The stand according to claim 2, further comprising first coded means connected to said remote control means for determining an actual position of said first counterweight relative to said first balancing arm and generating a first position signal representative of said actual position of said first counterweight.

4. The stand according to claim 3, wherein said memory stores load change information entered by a user, and said remote control means calculates a calibrated balancing position for said first counterweight based on said first position signal and said load change information, and actuates said first positioning means to move said first counterweight to said calibrated balancing position.

5. The stand according to claim 2, further comprising first coded means connected to said remote control means for determining an actual position of said first counterweight relative to said first balancing arm and generating a first position signal representative of said actual position of said first counterweight, and second coded means connected to said remote control means for determining an actual position of said second counterweight relative to said second balancing arm and generating a second position signal representative of said actual position of said second counterweight.

6. The stand according to claim 5, wherein said memory stores load change information entered by a user, and said remote control means calculates calibrated balancing positions for both said first and second counterweights based on said first and second position signals and said load change information, and actuates said first and second positioning means to move said first and second counterweights to said calibrated balancing positions.

7. The stand according to claim 2, wherein said signal from said measuring means represents imbalance of said load about a pivot axis of said first pivot means, said remote control means evaluates said signal to provide a balancing position for said first counterweight based on said signal, and said remote control means obtains a balancing position for said second counterweight based on said stored relationship.

8. The stand according to claim 1, wherein said measuring means includes a torque measuring device.

9. The stand according to claim 8, wherein said torque measuring device is operable about said horizontal axis of said first pivot means.

10. The stand according to claim 9, wherein said torque measuring device includes brake means for preventing pivotal motion of said load arm and said first balancing arm about said horizontal axis of said first pivot means.

11. The stand according to claim 10, wherein said brake means includes an electromagnet, and said brake means is actuated by progressively de-energizing said electromagnet.

12. The stand according to claim 1, wherein said measuring means includes a bending moment measuring device.

13. The stand according to claim 12, wherein said bending moment measuring device is located on said load arm.

14. The stand according to claim 1, wherein said measuring means includes a pressure sensing device under said foot and an angular displacement measuring device at said first pivot means.

15. The stand according to claim 1, wherein said first and second positioning means are variable to move said first and second counterweights at a variety of speeds depending upon said signal.

16. The stand according to claim 15, wherein said first positioning means moves said first counterweight at a first speed, said second positioning means moves said second counterweight at a second speed, and said first speed is different than said second speed.

17. The stand according to claim 1, wherein said load arm and said first balancing arm are parallel guide linkages.

18. The stand according to claim 17, further including another parallel guide linkage for transferring motion between said load arm and said first balancing arm.

19. The stand according to claim 1, wherein said remote control means includes a delay circuit to provide a time delay before evaluating said signal and actuating said first and second positioning means.

20. The stand according to claim 1, wherein said load arm, said upper tilting portion, said first balancing arm, and said second balancing arm are formed of a fiber-reinforced composite material.

21. The stand according to claim 1, wherein said pedestal is telescoping to permit height adjustment.

22. The stand according to claim 1, wherein said foot includes a plurality of supporting wheels, and at least one of said plurality of supporting wheels is retractable at least partially within a housing of said foot.

23. The stand according to claim 1, wherein said lower non-tilting portion of said pedestal is mounted on said foot by a transverse roller bearing to permit rotation of said pedestal with respect to said foot about a said vertical axis.

24. The stand according to claim 1, wherein said load arm is identical in shape to said upper tilting portion.

25. A method for balancing loading changes with respect to a load supported by a counter-balanced stand, said stand including a vertically extending pedestal having a lower non-tilting portion and an upper tilting portion pivotally connected to said lower non-tilting portion, a load arm pivotally connected to said upper tilting portion, a first balancing arm paired with said load arm, and a second balancing arm paired with said upper tilting portion, said method comprising the steps of:

providing a first counterweight supported by said first balancing arm for movement relative to a first pivot point between said load arm and said upper tilting portion, and providing a second counterweight supported by said second balancing arm for movement relative to a second pivot point between said upper tilting portion and said lower non-tilting portion;

storing a predetermined balancing relationship between said first and second counterweights;

measuring imbalance due to changes in said load and generating a signal representative of said imbalance; and automatically moving said first counterweight to a balancing position based on said signal, and automatically moving said second counterweight to another balancing position based on said stored balancing relationship wherein said first and second counterweights are moved at various speeds depending upon said signal.

26. The method according to claim 25, wherein the step of measuring imbalance includes detecting a torque about said first pivot point.

27. The method according to claim 26, wherein pivotal motion between said load arm and said upper tilting portion is braked during detection of said torque.

28. The method according to claim 25, wherein the step of measuring imbalance includes detecting a bending moment in said load arm.

29. The method according to claim 28, wherein pivotal motion between said load arm and said upper tilting portion is braked during detection of said bending moment.

* * * * *